US010932955B2

(12) United States Patent
Hamamoto

(10) Patent No.: US 10,932,955 B2
(45) Date of Patent: Mar. 2, 2021

(54) PERCUTANEOUS ABSORPTION AGENT DELIVERY DEVICE AND MANUFACTURING METHOD THEREFOR

(71) Applicant: MEDRX CO., LTD., Higashikagawa (JP)

(72) Inventor: Hidetoshi Hamamoto, Higashikagawa (JP)

(73) Assignee: MEDRX CO., LTD., Higashikagawa (JP)

( * ) Notice: Subject to any disclaimer, the term of this patent is extended or adjusted under 35 U.S.C. 154(b) by 39 days.

(21) Appl. No.: 15/774,441

(22) PCT Filed: Nov. 9, 2016

(86) PCT No.: PCT/JP2016/083247
§ 371 (c)(1),
(2) Date: May 8, 2018

(87) PCT Pub. No.: WO2017/082301
PCT Pub. Date: May 18, 2017

(65) Prior Publication Data
US 2018/0318567 A1 Nov. 8, 2018

(30) Foreign Application Priority Data

Nov. 12, 2015 (JP) .............................. JP2015-221975

(51) Int. Cl.
*A61F 13/02* (2006.01)
*A61K 9/70* (2006.01)
(Continued)

(52) U.S. Cl.
CPC ........ *A61F 13/02* (2013.01); *A61F 13/00063* (2013.01); *A61F 13/00072* (2013.01);
(Continued)

(58) Field of Classification Search
None
See application file for complete search history.

(56) References Cited

U.S. PATENT DOCUMENTS 4,781,293 A * 11/1988 Johns ..................... A61F 13/023
206/441
2004/0192714 A1* 9/2004 Boer ..................... C07D 489/12
514/279
(Continued)

FOREIGN PATENT DOCUMENTS

JP 48-94190 U 11/1973
JP 57-17614 U 1/1982
(Continued)

OTHER PUBLICATIONS

International Search Report (PCT/ISA/210) dated Feb. 14, 2017, by the Japanese Patent Office as the International Searching Authority for International Application No. PCT/JP2016/083247.
(Continued)

*Primary Examiner* — Isis A Ghali
(74) *Attorney, Agent, or Firm* — Buchanan Ingersoll & Rooney PC

(57) ABSTRACT

A percutaneous absorption agent delivery device with: a solvent-impermeable cover film that has a first layer and a second layer, which are integrally continuous via a first fold and are superimposed, a non-seal region and a seal region are formed between the first layer and the second layer, the non-seal region disposed along the first fold, the seal region to surround the outer peripheral section of the non-seal region except for the section along the first fold, and an endless cut portion forming the non-seal region formed in the cover film; a percutaneous absorption agent carrying member is disposed in the non-seal region between the first layer and the second layer, and fixed to the cover film on the inner side of the cut portion; and an adhesive sheet that is detachably affixed to the outer surface of the cover film.

15 Claims, 15 Drawing Sheets

(51) Int. Cl.
  *A61F 15/00* (2006.01)
  *A61F 13/00* (2006.01)
  *B32B 5/02* (2006.01)
  *B32B 7/06* (2019.01)
  *B32B 7/12* (2006.01)
  *B32B 27/08* (2006.01)
  *B32B 27/12* (2006.01)

(52) U.S. Cl.
  CPC ........ *A61F 13/0289* (2013.01); *A61F 15/001* (2013.01); *A61K 9/70* (2013.01); *A61K 9/7084* (2013.01); *B32B 5/02* (2013.01); *B32B 7/06* (2013.01); *B32B 7/12* (2013.01); *B32B 27/08* (2013.01); *B32B 27/12* (2013.01); *A61F 2013/0296* (2013.01); *A61M 2207/00* (2013.01); *B32B 2535/00* (2013.01)

(56) References Cited

U.S. PATENT DOCUMENTS

| | | | |
|---|---|---|---|
| 2006/0000734 A1 | 1/2006 | Ninomiya et al. | |
| 2008/0172015 A1 | 7/2008 | Okada et al. | |
| 2009/0011159 A1 | 1/2009 | Okada et al. | |
| 2014/0303574 A1* | 10/2014 | Knutson | A61F 13/0259 604/307 |

FOREIGN PATENT DOCUMENTS

| | | | |
|---|---|---|---|
| JP | 7-48249 A | | 2/1995 |
| JP | 2006-44793 A | | 2/2006 |
| JP | 3973420 B2 | | 9/2007 |
| JP | 4262934 B2 | | 5/2009 |
| JP | 4335317 B2 | | 9/2009 |
| JP | 2010-155810 A | | 7/2010 |
| JP | 2010155810 A | * | 7/2010 |
| JP | 4879442 B2 | | 2/2012 |
| JP | 4975534 B2 | | 7/2012 |
| JP | 5059584 B2 | | 10/2012 |
| WO | WO 98/13000 A1 | | 4/1998 |
| WO | WO 01/91848 A2 | | 12/2001 |

OTHER PUBLICATIONS

International Preliminary Report on Patentability and Written Opinion of the International Searching Authority (Forms PCT/IB/338, PCT/IB/373 and PCT/ISA/237) dated May 24, 2018, by the International Bureau of WIPO, in corresponding International Application No. PCT/JP2016/083247. (6 pages).

* cited by examiner

PERCUTANEOUS ABSORPTION AGENT DELIVERY DEVICE AND MANUFACTURING METHOD THEREFOR

TECHNICAL FIELD

The present invention relates to a percutaneous absorption agent delivery device and a manufacturing method therefore.

BACKGROUND ART

A percutaneous absorption agent delivery device has hitherto been known that, with a pressure-sensitive adhesive sheet, retains on skin a percutaneous absorption agent carrying member carrying a material having medicinal ingredients as a percutaneous absorption agent.

For example, Patent Document 1 discloses a wound dressing. The wound dressing includes a lining material; a pressure-sensitive adhesive layer coated on part of the lining material; and an absorptive web attached to the lining material by adhesive means in order to provide voids to exudate emanating from the wound; the pressure-sensitive adhesive layer containing antimicrobials that restrain microorganisms from entering the web from the external environment.

Patent Document 2 discloses an iontophoresis delivery device for drugs. The device includes a backing (closure) having a recess; a drug absorption substance stored in the recess; a web adhered peelably to the backing so as to cover the recess; and a reservoir fitted to an inner surface of the web to allow a drug aliquot absorbed in the drug absorption substance to be absorbed by a patient contact surface.

Patent Document 3 discloses a wound dressing to cover and protect a wound surface of a body. The wound dressing includes a pressure-sensitive adhesive supporting member made of e.g. a film or a non-woven fabric; and a pressure-sensitive adhesive layer and a hydrogel layer that are disposed on one surface of the pressure-sensitive adhesive supporting member, the hydrogel layer being affixed to the pressure-sensitive adhesive layer.

Moreover, Patent Documents 4 to 6 also disclose a percutaneous absorption agent delivery device having similar configurations.

PRIOR ART DOCUMENT

Patent Document

Patent Document 1: JP4335317B
Patent Document 2: JP4879442B
Patent Document 3: JP3973420B
Patent Document 4: JP4262934B
Patent Document 5: JP5059584B
Patent Document 6: JP4975534B

SUMMARY OF THE INVENTION

Problem to be Solved by the Invention

An object of the present invention is to provide a novel percutaneous absorption agent delivery device having configurations different from those of the various types of percutaneous absorption agent delivery devices described above, and a method for manufacturing the same.

Means for Solving Problem

A percutaneous absorption agent delivery device according to an aspect of the present invention comprises:

(a) a solvent-impermeable cover film (10) having a first layer part (11) and a second layer part (12) that are integrally continuous via a first fold (13) and are superimposed on each other, with a non-sealed region (15) and a sealed region (14) being formed between the first layer part and the second layer part, the non-sealed region (15) being arranged along the first fold (13), the sealed region (14) being arranged so as to surround an outer periphery of the non-sealed region (15) other than portions along the first fold, with an endless cut part (17) being formed at portions defining the non-sealed region;

(b) a percutaneous absorption agent carrying member (20, 120, 220) arranged between the first layer part (11) and the second layer part (12) in the non-sealed region (15), the percutaneous absorption agent carrying member (20, 120, 220) being secured to the cover film (10) inside of the cut part (17); and (c) a pressure-sensitive adhesive sheet (30) adhered peelably to an outer surface of the cover film (10).

A method for manufacturing a percutaneous absorption agent delivery device according to an aspect of the present invention comprises:

a step 1 of feeding a solvent-impermeable cover film;
a step 2 of forming an endless cut part in the cover film;
a step 3 of arranging a percutaneous absorption agent carrying member on one surface of the cover film;
a step 4 of securing the percutaneous absorption agent carrying member to the cover film;
a step 5 of allowing the percutaneous absorption agent carrying member to carry a drug;
a step 6 of folding the cover film along a predetermined fold and inserting the percutaneous absorption agent carrying member between a first film part formed on one side of the cover film across the fold and a second film part formed on the other side thereof;
a step 7 of providing a seal between the first film part and the second film part in a region surrounding an outer periphery of the percutaneous absorption agent carrying member other than portions facing the fold; and
a step 8 of peelably adhering the pressure-sensitive adhesive sheet to an outer surface of the cover film in portions covering at least the cut part.

Effect of the Invention

According to a percutaneous absorption agent delivery device of the present invention and to a percutaneous absorption agent delivery device manufactured by a manufacturing method of the present invention, the percutaneous absorption agent carrying member is stored between the first layer part and the second layer part of the folded cover film, with the space between the first layer part and the second layer part being sealed around the percutaneous absorption agent carrying member. As a result, a liquid agent carried on the percutaneous absorption agent carrying member is hermetically sealed, making it possible to prevent the liquid agent from leaking or volatilizing and diffusing in the distribution process.

Since the seal region may not be formed at the portion along the fold between the first layer part and the second layer part of the cover film, the seal region can be reduced as compared with the case where the entire circumference of the percutaneous absorption agent carrying member is surrounded by the seal region. Hence, the percutaneous absorption agent delivery device can be made compact, achieving an improvement in the portability.

In use of the percutaneous absorption agent delivery device of the present invention, the cover film is partly peeled off from the pressure-sensitive adhesive sheet. At this time, the cover film breaks at the cut part so that the inside region of the cover film surrounded by the cut part remains left together with the percutaneous absorption agent carrying member on the pressure-sensitive adhesive sheet. Accordingly, irrespective of the direction of the percutaneous absorption agent delivery device upon unsealing, the percutaneous absorption agent carrying member cannot peel off from the pressure-sensitive adhesive sheet. Thus, similar to the general patches, a sheet of film is only peeled off so that it can easily be affixed onto skin.

In the case where the percutaneous absorption agent carrying member is stored in the space between two films (a film carrying the percutaneous absorption agent carrying member and a peel-off film), the entirety of the film (peel-off film) on one hand and part of the film (film carrying the percutaneous absorption agent carrying member) on the other are peeled away from the pressure-sensitive adhesive sheet in use and discarded. At this time, the liquid agent permeating in the percutaneous absorption agent carrying member adheres to the peeled-away peel-off film, and therefore, if the peel-off film is discarded, the liquid agent adhered thereto becomes waste. On the contrary, due to the absence of the peel-off film in the delivery device of the present invention, no liquid agent is wasted. In use of the delivery device of the present invention, only part of the one sheet of film is discarded. Although all of the sealed portions of the cover film are discarded at that time, the size of the sealed portions is reduced because the film portions along the folds are not sealed as described above. Accordingly, the film portions to be discarded in use can be reduced, leading to curtailed material costs.

In this manner, the percutaneous absorption agent delivery device of the present invention can expand the available field of liquid agents as a novel device for the liquid agents and can develop novel applications of the liquid agents.

MODES FOR CARRYING OUT THE INVENTION

Reference will now be made to the accompanying drawings to describe embodiments of a percutaneous absorption agent delivery device (hereinafter, referred to simply as "device") according to the present invention and a method for manufacturing the same.

1-1. Overall Structure

Figure 1:
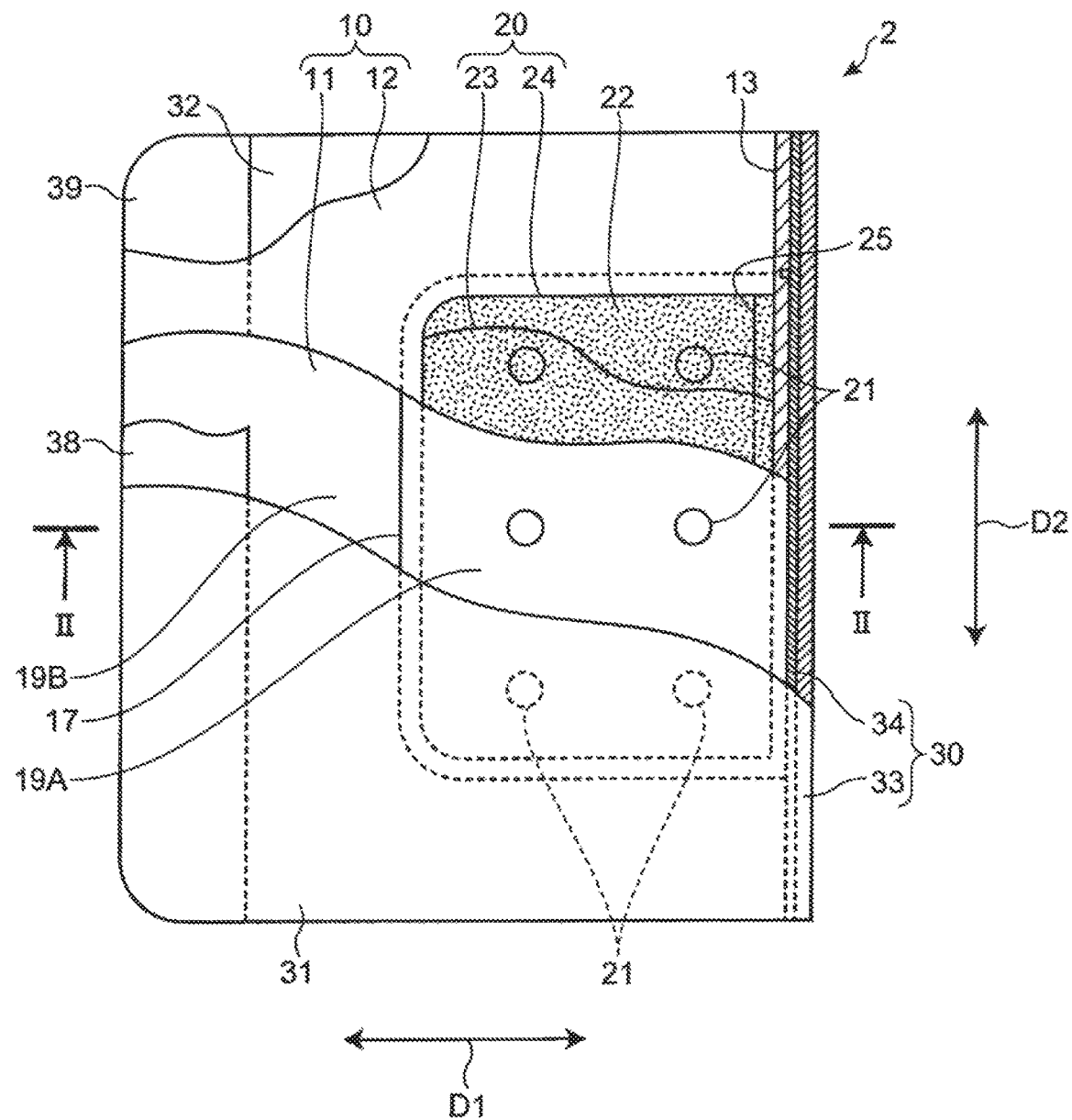
FIG. 1 is a partially cut-away plan view of a percutaneous absorption agent delivery device according to the present invention.
Figure 2:
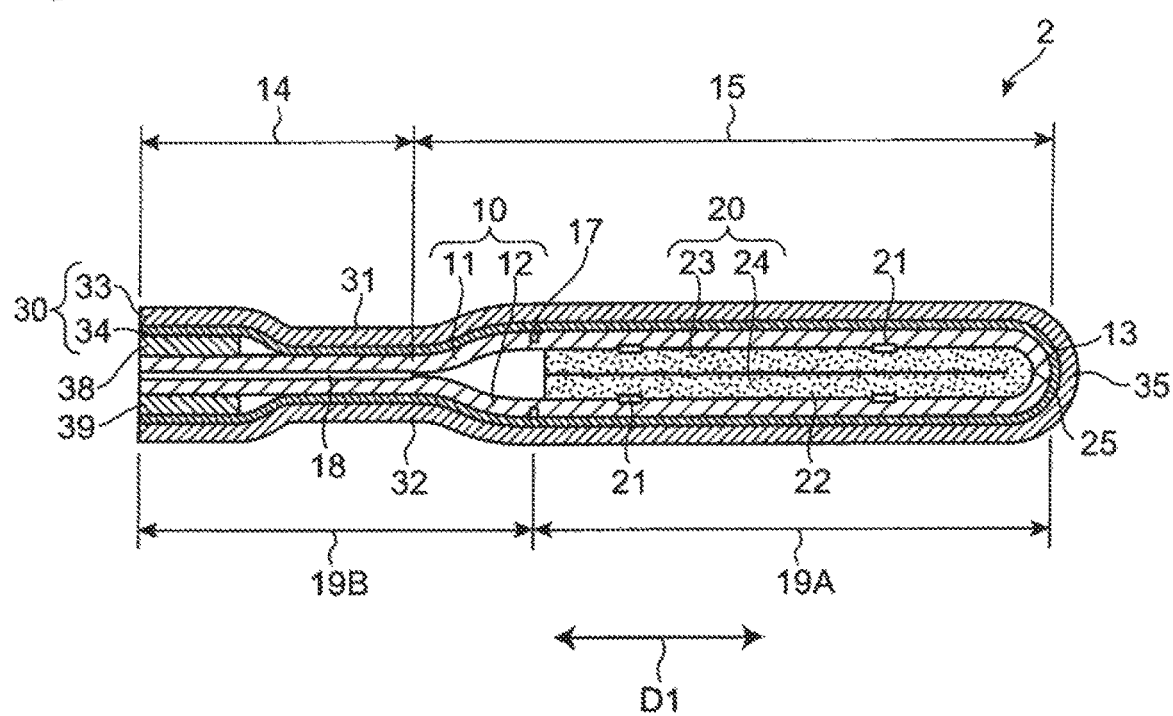
FIG. 2 is a sectional view taken along line II-II of FIG. 1, schematically showing the percutaneous absorption agent delivery device of FIG. 1.

Referring to FIGS. 1 and 2, the device is generally designated at reference numeral 2 and includes a plurality of laminated sheets or films. In an embodiment, the device 2 comprises as its main part a cover film 10 and a pressure-sensitive adhesive sheet 30. As shown in FIG. 1, a planar shape of the device 2 is a quadrangle having a pair of sides extending in a first direction D1 and a pair of sides extending in a second direction D2 orthogonal to the first direction D1. It is to be noted that the planar shape of the device 2 is not limited thereto and that it may be a circle, an ellipse, or other polygons.

1-2. Cover Film

The cover film 10 is preferably formed from a plastic sheet, film, or laminated film that is made of a solvent-impermeable material, and the material is not particularly limited as long as it is used in a normal heat seal. Examples of a specific material include polyolefins such as polyethylene and polypropylene; polyesters such as polyethylene terephthalate, polybutylene terephthalate, and polyethylene naphthalate; polyvinyl chloride; polyvinylidene chloride; polyamide such as nylon-6 and nylon-66; polyimide; ethylene vinyl alcohol; and copolymers of these polymers as well. Preferably, an aluminum laminate film is used as the sheet or film made of a plastic sheet or plastic film material, the aluminum laminate film being in the form of, e.g. a composite material with an aluminum foil interposed between front and back plastic layers or a composite material with a plastic layer deposited with aluminum being interposed between the front and back plastic layers.

At least outer surface of the cover film 10 is preferably coated with a peel-off agent. The peel-off agent may be a silicon-based peel-off agent or a non-silicon-based peel-off agent such as a fluorine-based peel-off agent.

With the rectangular film being folded in two, the cover film 10 is sealed on three sides. At a center in the first direction D1 in the unfolded state, the cover film 10 is folded back along a fold (first fold) 13 extending in the second direction D2. As a result, an upper layer part (first layer) arranged on the upper side of FIG. 2 forms on one side with respect to the fold 13 of the cover film 10, while a lower layer part (second layer) arranged on the lower side of FIG. 2 forms on the other side. The upper layer part 11 and the lower layer part 12 are integrally continuous via the fold 13 and are superimposed together. Preferably, the upper layer part 11 and the lower layer part 12 have the same planar shape and the same size and are superimposed together over the entire surface.

Figure 3:
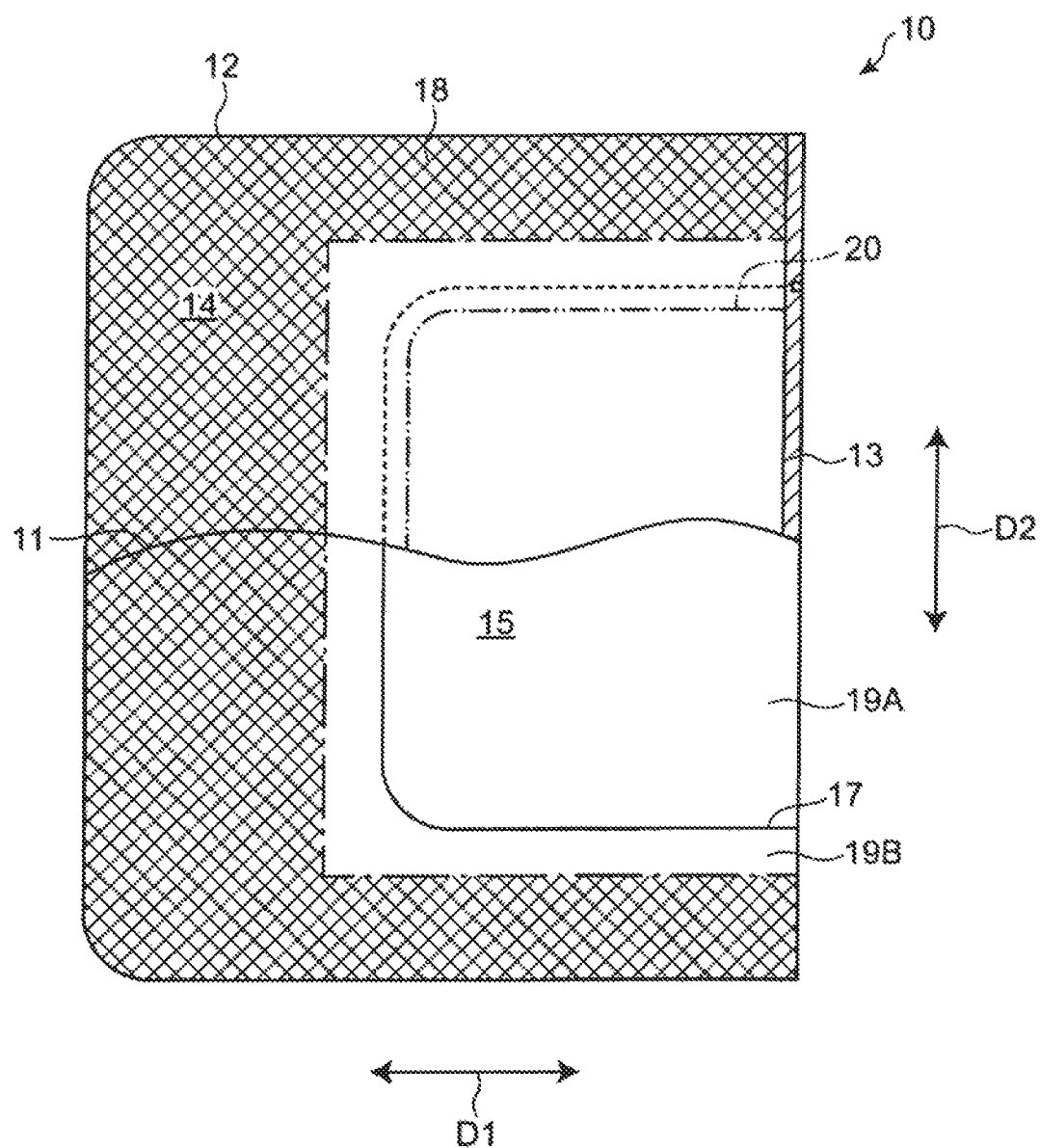
FIG. 3 is a diagram showing a sealed region and a non-sealed region of a cover film in the percutaneous absorption agent delivery device of FIG. 1.

As shown in FIG. 3, a sealed region 14 and a non-sealed region 15 are formed between the upper layer part 11 and the lower layer part 12 of the cover film 10. In FIG. 3, the sealed region 14 is a region with a check pattern and the non-sealed region 15 is a remaining region of the cover film 10.

Although the non-sealed region 15 is a quadrangular region for example, the shape of the non-sealed region 15 is not particularly limited thereto and may be semicircular for example. The non-sealed region 15 has dimensions smaller than those of the upper layer part 11 and the lower layer part 12 in the first direction D1 and the second direction D2. The non-sealed region 15 is arranged toward the fold 13 of the cover film 10 in the first direction D1, whereas it is arranged at the center portion of the cover film 10 in the second direction D2. More specifically, in the first direction D1, an edge on one side of the non-sealed region 15 is arranged along the fold 13, whereas an edge on the other side thereof is arranged closer to the center than edges of the upper layer part 11 and the lower layer part 12. In the second direction D2, edges on both sides of the non-sealed region 15 are arranged closer to the center than edges of the upper layer part 11 and the lower layer part 12.

The sealed region 14 is for example a U-shaped region defined by a three-sided seal. In the sealed region 14, the upper layer part 11 and the lower layer part 12 are adhered and sealed by a heat seal 18. The sealed region 14 is disposed adjoining the non-sealed region 15 on opposite sides to the fold 13 in the first direction D1 and on both sides in the second direction D2. This allows the sealed region 14 to continuously surround the outer periphery of the non-sealed region 15 other than the portion along the fold 13. The non-sealed region 15 is surrounded over the entire circumference by the thus formed sealed region 14 and the fold 13 so that a hermetically sealed space is formed within the non-sealed region 15.

As shown in FIGS. 1 to 3, the cover film 10 includes an endless cut part 17. This partitions the cover film 10 into an inside region 19A surrounded by the cut part 17 and an outside region 19B located outside of the cut part 17. In the unfolded state of the cover film 10, the cut part 17 extends across portions corresponding to the upper layer part 11 and portions corresponding to the lower layer part 12. In the unfolded state of the cover film 10, the cut part 17 has a planar shape of a quadrangle for example. Note that the planar shape of the cut part 17 in the unfolded state of the cover film 10 is not particularly limited as long as it is endless and, for example, it may be an annular shape such as ellipse and oval.

The cut part 17 is formed at portions of the cover film 10 that form the non-sealed region 15. In the folded state of the cover film 10, the cut part 17 is disposed along a boundary between the non-sealed region 15 and the sealed region 14.

The cut part 17 may be a continuous cut or may be intermittent perforations. The cut part 17 may be a so-called full cut that extends from one surface up to the other surface of the cover film 10 or may be a so-called half cut leaving without cutting a portion in the vicinity of one surface of the cover film 10. It is preferable for the full cut to be so-called perforations partially leaving uncut portions. In order to facilitate avoiding evaporation and scattering of the solvent of the percutaneous absorption drug, the cut part 17 is preferably the half cut. In the shown embodiment, the cut part 17 is the half cut extending from the outer surface up to the vicinity of the inner surface of the cover film 10.

1-3. Percutaneous Absorption Agent Carrying Member

As shown in FIGS. 1 and 2, a percutaneous absorption agent carrying member (hereinafter, referred to as "carrying member") 20 is disposed between the upper layer part 11 and the lower layer part 12 in the non-sealed region 15 of the cover film 10. The carrying member 20 is fixed in the inside region 19A of the cover film 10 by a heat-bonded part 21. The heat-bonded part 21 is formed by spot welding, and the carrying member 20 has a plurality of heat-bonded parts 21 interspersed thereon.

The carrying member 20 is not particularly limited as long as it is a member that can be stably impregnated with and hold a liquid or paste-like percutaneous absorption drug (hereinafter, referred to as "drug") 22. For example, the material thereof can be absorbent cottons; cotton fabrics such as gauze; nonwoven fabrics; synthetic fiber fabrics made of polyester, polyethylene, polyvinyl, etc.; sponge; or paper. The sponge can be synthetic sponge such as urethane foam; or natural sponge. In any case, the material of the carrying member 20 may be selected as optimum depending on the type of the drug 22 carried thereon.

Folded in half, the carrying member 20 is stored between the upper layer part 11 and the lower layer part 12 of the cover film 10. In its unfolded state, the carrying member 20 is of a rectangular shape that has a pair of sides extending in the first direction D1 and a pair of sides extending in the second direction D2. It should be noted that the shape of the unfolded carrying member 210 is not particularly limited thereto but can be for example a circle, an ellipse, or polygons other than the quadrangle.

At the center in the first direction D1 in its unfolded state, the carrying member 20 is folded back along a fold (second fold) 25 extending in the second direction D2. As a result, an upper layer part (third layer part) 23 arranged on the upper side of FIG. 2 forms on one side across the fold 25 of the carrying member 20, whereas a lower layer part (fourth layer part) 24 arranged on the lower side of FIG. 2 forms on the other side. Preferably, the upper layer part 23 and the lower layer part 24 are integrally continuous via the fold 25 and are superimposed together. The upper layer part 23 and the lower layer part 24 have the same planar shape and the same size and are superimposed together over the entire surface.

The fold 25 of the carrying member 20 runs along the fold 13 of the cover film 10. The upper layer part 23 of the carrying member 20 is superimposed on the inner surface of the upper layer part 11 of the cover film 10 in the inside region 19A, the upper layer part 23 being secured to the upper layer part 11 by the heat-bonded parts 21. The lower layer part 24 of the carrying member 20 is superimposed on the inner surface of the lower layer part 12 of the cover film 10 in the inside region 19A, the lower layer part 24 being secured to the lower layer part 12 by the heat-bonded parts 21.

The configuration of the adhesion parts between the carrying member 20 and the cover film 10 is not particularly limited to those interspersed at a plurality of locations, but for example a linearly extending adhesion part(s) or a planarly extending adhesion part(s) may be formed at a single or a plurality of locations.

The drug 22 is a liquid-like, gel-like, or paste-like material having medicinal ingredients as the percutaneous absorption drug. For example, it can be an aqueous solution or organic solvent in which the medicinal ingredients are dissolved. The organic solvent is not particularly limited as long as it is usable for a percutaneous absorption patch. It can include an organic ionic liquid that is a solvent having a strong dissolving power. It can also include a mixture thereof. The organic solvent can be for example fatty acid esters such as isopropyl palmitate, isopropyl myristate, cetyl lactate, diethyl sebacate, lauric acid hexyl, isooctane cetyl, lauryl lactate, and ethyl oleate; for example glycols such as ethylene glycol, propylene glycol, 1,3-butylene glycol, polyethylene glycol, polypropylene glycol, and glycerin; or for example alcohols such as ethanol, propanol, isopropanol, and butanol.

The organic ionic liquid can be Bronsted salt of liquid at normal temperature, formed by a fatty acid and an organic amine compound. The fatty acid and the organic amine compound are not particularly limited as long as they are usable for a patch. Examples of the former can include fatty acids such as levulinic acid, octanoic acid, decanoic acid, oleic acid, stearic acid, and isostearic acid, while examples of the latter can include lower alkyl amines such as diethanol amine, diisopropanol amine, triethanol amine, and triisopropanol amine.

The drug 22 may contain a percutaneous absorption accelerant added thereto. The percutaneous absorption accelerant can be for example higher alcohols such as cetanol, stearyl alcohol, lauryl alcohol, cetostearyl alcohol, myristyl alcohol, and oleyl alcohol; menthol; or limonene. Furthermore, one or more may be used for example that are selected from the group consisting of ester solvents such as isopropyl myristate, isopropyl palmitate, diethyl sebacate, and propylene carbonate; and N-methyl-2-pyrrolidon. A surfactant can also be used, and the surfactant can be a nonionic surfactant, an anionic surfactant, a cationic surfactant, or an amphoteric surfactant. Examples of the nonionic surfactant include sorbitan monolaurate, sorbitan monopalmitate, sorbitan sesquioleate, glycerin monostearate, decaglyceryl monolaurate, hexaglycerin polyricinoleate, polyoxyethylene(9)lauryl ether, polyoxyethylene(2)lauryl ether, polyoxyethylene(4,2)lauryl ether, polyoxyethylene(5) nonylphenyl ether, polyoxyethylene (7,5)nonylphenyl ether, polyoxyethylene(10)nonylphenyl ether, polyoxyethylene(3) octylphenyl ether, polyoxyethylene(10)octylphenyl ether, polyoxyethylene(10)oleylamine, polyoxy(5)oleylamine, polyoxy(5)oleamide, polyoxyethylene(2)monolaurate, stearic acid monoglyceride, and polyoxyethylene castor oil (hardened castor oil).

Examples of the anionic surfactant include sodium lauryl sulfate, potassium lauryl sulfate, triethanolamine lauryl sulfate, sodium cetyl sulfate, sodium lauroyl sarcosinate, sodium di-2-ethylhexyl sulfosuccinate, sodium polyoxyethylene(10)lauryl ether phosphate, sodium polyoxyethylene (4)lauryl ether phosphate, sodium polyoxyethylene(5)cetyl ether phosphate, and sodium polyoxyethylene(6)oleylether phosphate.

Examples of the cationic surfactant include stearyltrimethylammonium chloride, distearyldimethylammonium chloride, benzalkonium chloride, and stearyldimethylbenzylammonium chloride.

Examples of the amphoteric surfactant include phosphatidylcholine, lauryldimethylaminoacetic acid betaine, and 2-alkyl-N-carboxymethyl-N-hydroxyethylimidazolinium betaine. Other than the above, lauroyldiethanolamide is also usable.

The "medicinal ingredients" are not particularly limited as long as they are medicinal ingredients usable as the percutaneous absorption drug, but can be for example nonsteroidal anti-inflammatory drugs (NSAID) such as indomethacin, flurbiprofen, ketoprofen, and diclofenac; local anesthetics such as lidocaine and dibucaine; tramadol, eperisone, ramelteon, donepezil, escitalopram, galanthamine, ramelteon, morphine, oxycodone, paroxetine, ropinirole, pergolide, ondansetron, raloxifene, rochigonin, aripiprazole, fentanyl, apomorphine, memantine, amantadine, tulobuterol, tolbutamide, glibenclamide, oxybutynin, neostigmine, nicardipine, dopamine, etc. Furthermore, combinations of these medicinal ingredients are also usable. Medicinal ingredients turned into ionic liquid as a result of combination of acid and base are also usable. A preferred combination can be for example combination of the above NSAID as acid and local anesthetics as base.

The "solvent" refers to an aqueous solution or the organic solvent for dissolving medicinal ingredients. The organic solvent refers to one containing the percutaneous absorption accelerant. That is, the organic solvent is not particularly limited as long as it is usable for the percutaneous absorption patch. It includes the organic ionic liquid that is a solvent with a strong dissolving power. Mixtures thereof are also included therein.

1-4 Pressure-Sensitive Adhesive Sheet

As shown in FIGS. 1 and 2, the pressure-sensitive adhesive sheet 30 comprises a base layer 33 and a pressure-sensitive adhesive layer 34 disposed on a surface (inner surface) of the base layer 33 that confronts a cover film 10. The pressure-sensitive adhesive layer 34 is disposed on the entire inner surface of the base layer 33.

The base layer 33 is formed from a nonwoven fabric, a woven fabric, a synthetic resin sheet, or a composite thereof. Materials of the base layer 33 can be for example polyethylene, polypropylene, polycarbonate, polyesters, polyamide, polyvinyl chloride, cotton, urethane, etc., and additionally, a composite thereof.

The pressure-sensitive adhesive layer 34 is made of a pressure-sensitive adhesive that can exhibit an adhesive force required between it and an outer surface of the cover film 10. If the cut part 17 of the cover film 10 is fully cut, a pressure-sensitive adhesive is preferably used that can prevent the drug 22 carried on the carrying member 20 from leaking to the outside through an interface between the cover film 10 and the pressure-sensitive adhesive layer 34. Specifically, an acrylic, synthetic-rubber-based, or natural-rubber-based pressure-sensitive adhesive may appropriately be selected for use. A preferred one can be an acrylic pressure-sensitive adhesive having as its main component a copolymer of acrylic monomers such as 2-ethylhexyl acrylate, butyl acrylate, ethyl acrylate, and methyl methacrylate or can be a synthetic-rubber-based pressure-sensitive adhesive in the form of e.g. styrene-isoprene-styrene copolymer (SIS) and a tackifier such as terpene resin. In order to improve the liquid resistance, a trimellitate ester-based plasticizer or a polyester-based plasticizer may be used as a plasticizer at the same time.

The pressure-sensitive adhesive layer 34 of the pressure-sensitive adhesive sheet 30 is adhered peelably to the outer surface of the cover film 10. Thus, the pressure-sensitive adhesive layer 34 and the base layer 33 are laminated in the mentioned order on the outside of the cover film 10. The pressure-sensitive adhesive sheet 30 comprises a fold-back part 35 at which the sheet is folded back along the fold 13 of the cover film 10. The pressure-sensitive adhesive sheet 30 comprises a top part 31 formed on one side across the fold-back part 35 as a first surface part configuring one surface of the device 2, and a bottom part 32 formed on the other side as a second surface part configuring the other surface of the device 2. The top part 31 is adhered to the outer surface of the upper layer part 11 of the cover film 10, whilst the bottom part 32 is adhered to the outer surface of the lower layer part 12 of the cover film 10.

The pressure-sensitive adhesive sheet 30 is disposed so as to cover the entire outer surface of the cover film 10. The pressure-sensitive adhesive sheet 30 may be disposed so as to partially cover the outer surface of the cover film 10 as long as it covers at least the inside region 19A of the cover film 10.

1-5. Peel-Off Film

As shown in FIGS. 1 and 2, it is preferred that the pressure-sensitive adhesive sheet 30 have, at its outer peripheral edge, peel-off films 38 and 39 interposed between the cover film 10 and the pressure-sensitive adhesive sheet 30. The peel-off films 38 and 39 are adhered peelably to the pressure-sensitive adhesive layer 34 of the pressure-sensitive adhesive sheet 30.

In the shown example, the peel-off films 38 and 39 are interposed, respectively, between the top part 31 of the pressure-sensitive adhesive sheet 30 and the upper layer part 11 of the cover film 10 and between the bottom part 32 of the pressure-sensitive adhesive sheet 30 and the lower layer part 12 of the cover film 10. The peel-off films 38 and 39 are formed like belts each extending in the second direction D2 and are arranged along edges opposite to the fold-back part 35 in the top part 31 and the bottom part 32 of the pressure-sensitive adhesive sheet 30.

The peel-off film 38, 39 may be disposed on only either the top part 31 or the bottom part 32. In a state of being folded along a fold extending in the longitudinal direction, the peel-off films 38 and 39 may be arranged between the cover film 10 and the pressure-sensitive adhesive sheet 30.

Although not particularly limited, the material of the peel-off films 38 and 39 can be for example polyethylene, polypropylene, polyester, etc. In order to facilitate peeling from the adhesive mass, the surface of the peel-off films 38 and 39 may be subjected to silicon processing.

2. Manufacturing Method

A manufacturing method of the device 2 having the above configurations will be described with reference to FIG. 4.

A manufacturing process comprises steps 1 to 10 which follow. The steps will hereinafter be described.

Step 1: Feeding Cover Film

Figure 4:
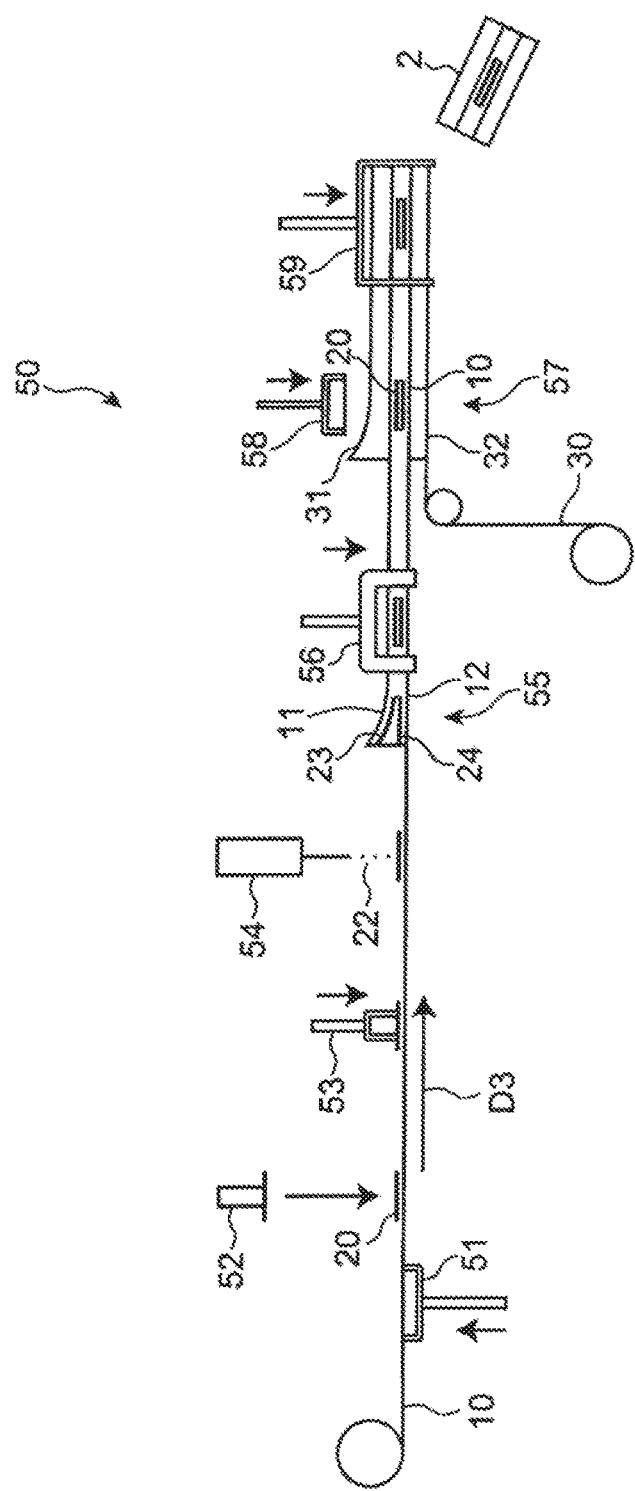
FIG. 4 is a diagram showing a manufacturing process of the percutaneous absorption agent delivery device of FIG. 1.

In a manufacturing process 50 shown in FIG. 4, the cover film 10 is fed continuously along a conveying direction D3 from the left toward the right of the diagram. The cover film 10 is conveyed in a posture where the second direction D2 (see FIGS. 1 and 3) is parallel to the conveying direction D3.

Step 2: Forming Cut Part

A cutter 51 is applied to the lower surface of the cover film 10 to form the cut part 17. Although not shown, a support table is disposed opposite to the cutter 51 across the cover film 10 so that the cut part 17 is formed on the cover film 10 sandwiched between the cutter 51 and the support table. As described above, the type of the cutter 51 is selected depending on the type (continuous cut, perforations, full cut, or half cut) of the cut part 17.

Step 3: Feeding Carrying Member

The carrying member 20 is placed on the upper surface of the cover film 10 by a carrying member feeder 52. At this time, the carrying member 20 is placed in the inside region 19A of the cover film 10.

Step 4: Fixing Carrying Member

The carrying member 20 and the cover film 10 are welded together at a plurality of locations by an ultrasonic spot welder 53 for example, to form the heat-bonded part 21.

Step 5: Feeding Drug

Drug 22 is fed from a drug feeder 54 to the carrying member 20.

Step 6: Folding Cover Film and Carrying Member

The cover film 10 and the carrying member 20 conveyed in the conveying direction D3 are folded along the folds 13 and 25 (see FIGS. 1 and 2) (extending in the conveying direction D3 (second direction D2) by a first folding mechanism 55 disposed on a conveyance path.

Step 7: Heat Sealing

Using a heat sealer 56, a heat seal 18 is applied in the outside region 19B to the pair of film portions (upper layer part 11 and lower layer part 12) formed on the cover film 10 by being folded. The heat seal 18 is a three-sided seal that seals three edges other than the fold 13 of the cover film 10, with the inside region 19A of the cover film 10 being not sealed. This allows the cover film 10 to have the U-shaped sealed region 14 and the non-sealed region 15 surrounded by the sealed region 14 and the fold 13, with the carrying member 20 being stored within a hermetically sealed space defined in the non-sealed region 15.

Step 8: Feeding Pressure-Sensitive Adhesive Sheet

In a posture of the pressure-sensitive adhesive layer 34 facing upward, the pressure-sensitive adhesive sheet 30 is fed to and superimposed on the underside of the folded cover film 10 storing the carrying member 20 so that the pressure-sensitive adhesive sheet 30 superimposed on the bottom of the cover film 10 is conveyed together with the cover film 10 along the conveying direction D3. The pressure-sensitive adhesive sheet 30 is folded back along the fold 13 of the cover film 10 extending in the conveying direction D3 (second direction D2) by a second folding mechanism 57 disposed on the conveyance path, so that the folded-back portion of the pressure-sensitive adhesive sheet 30 is superimposed on top of the cover film 10.

In the step 8, the pressure-sensitive adhesive sheet 30 may be fed that has the peel-off films 38 and 39 adhered previously to the edges of the pressure-sensitive adhesive layer 34, or the peel-off films 38 and 39 fed separately from the pressure-sensitive adhesive sheet 30 may be attached to the pressure-sensitive adhesive sheet 30 before it is folded back by the folding mechanism 57.

Step 9: Laminating

The cover film 10 covered by the pressure-sensitive adhesive sheet 30 is pressurized with a laminator 58 from above and below so that the pressure-sensitive adhesive layer 34 of the pressure-sensitive adhesive sheet 30 sticks to the outer surface of the cover film 10.

Step 10: Punching

A laminate consisting of a plurality of sheets or films laminated as above is punched by a punching cutter 59 that has a blade along the contour of the device 2. This punching is carried out on the outer periphery other than portions along the fold of the laminate.

Although in the above description the step 2 of forming the cut part 17 on the cover film 10 has been provided immediately before the step 3 of feeding the carrying member 20, the step 2 of forming the cut part 17 may be carried out at any time as long as it precedes the step 6 of folding the cover film 10 and the carrying member 20. For example, it may be carried out after the step 4 of fixing the carrying member 20 or after the step 5 of feeding the drug 22.

Although in the above description the step 8 of feeding the pressure-sensitive adhesive sheet 30 has been provided after the step 7 of performing the three-sided sealing, if the pressure-sensitive adhesive sheets 30 previously cut into small ones are intermittently fed, the intermittently fed pressure-sensitive adhesive sheets 30 may partially be overlaid on the outer surface of the cover film 10 and thereafter the three-sided sealing may be carried out on portions of the cover film 10 not having the pressure-sensitive adhesive sheets 30 overlaid thereon in a region along the outer edges of the pressure-sensitive adhesive sheets 30.

3. Use

Use of the thus manufactured device 2 will be described.

Figure 5A:
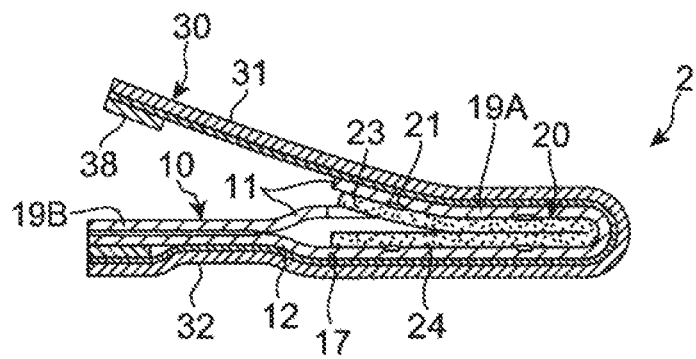
FIG. 5A is a diagram for explaining use of the percutaneous absorption agent delivery device of FIG. 1.

In use, as shown in FIG. 5A, an edge having the peel-off film 38 attached on the top part 31 for example of the pressure-sensitive adhesive sheet 30 is first grasped to peel away the top part 31 from the upper layer part 11 of the cover film 10. Since the cover film 10 is partitioned by the cut part 17 into the inside region 19A and the outside region 19B, the pressure-sensitive adhesive sheet 30 is peeled off from the outside region 19B in the upper layer part 11 of the cover film 10, whereas the inside region 19A of the upper layer part 11 is separated from the outside region 19B along the cut part 17 and remains left on the pressure-sensitive adhesive sheet 30. The carrying member 20 fixed to the inside region 19A of the cover film 10 also remains over the pressure-sensitive adhesive sheet 30 via the inside region 19A.

Figure 5B:
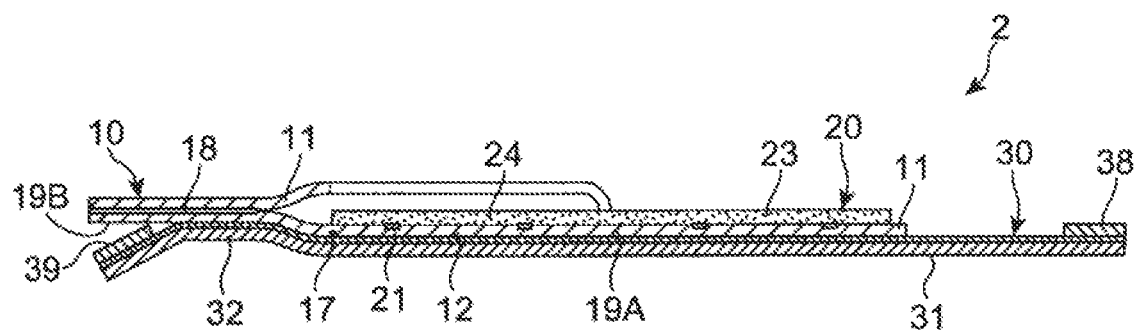
FIG. 5B is a diagram for explaining use of the percutaneous absorption agent delivery device of FIG. 1.
Figure 5C:
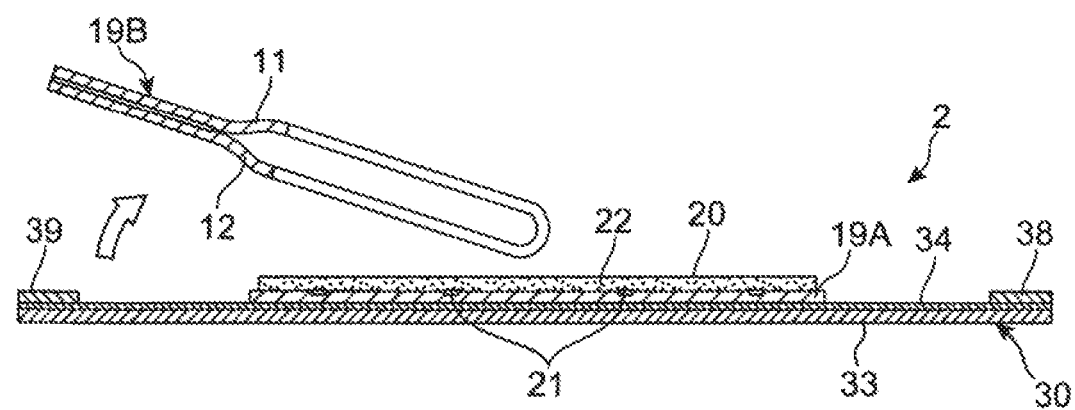
FIG. 5C is a diagram for explaining use of the percutaneous absorption agent delivery device of FIG. 1.

Next, as shown in FIG. 5B, an edge having the peel-off film 39 attached on the bottom part 32 of the pressure-sensitive adhesive sheet 30 is grasped to peel away the bottom part 32 from the lower layer part 12 of the cover film 10. As a result, as shown in FIG. 5C, the inside region 19A of the cover film 10 is separated from the outside region 19B over the entire circumference so that the entire outside region 19B is peeled off from the pressure-sensitive adhesive sheet 30. At this time, the entire inside region 19A of the cover film 10 and the entire carrying member 20 remain left over the pressure-sensitive adhesive sheet 30. The inside region 19A of the cover film 10 and the carrying member 20 are retained both in the unfolded state over the unfolded pressure-sensitive adhesive sheet 30.

Figure 5D:
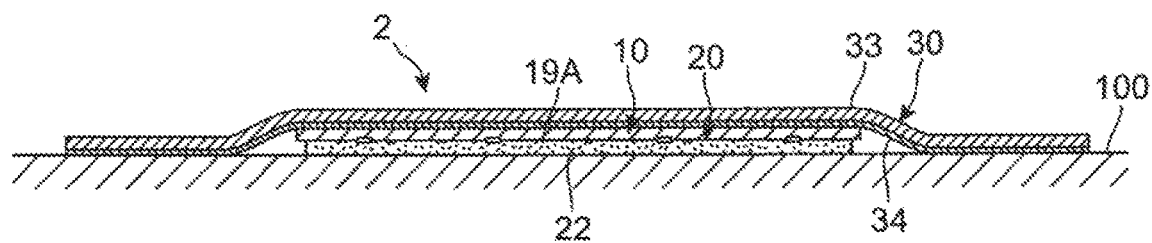
FIG. 5D is a diagram for explaining use of the percutaneous absorption agent delivery device of FIG. 1.

As shown in FIG. 5D, the device 2 with the outside region 19B of the cover film 10 removed is attached to a skin 100 with its pressure-sensitive adhesive layer 34 being placed thereon. Finally, the peel-off films 38 and 39 are peeled away from the pressure-sensitive adhesive layer 34 of the pressure-sensitive adhesive sheet 30, to attach the entire pressure-sensitive adhesive layer 34 to the skin 100.

When the pressure-sensitive adhesive sheet 30 is peeled away from the outside region 19B of the cover film 10, the inside region 19A needs to be separated from the outside region 19B along the cut part 17 while securely keeping the state where the inside region 19A of the cover film 10 sticks to the pressure-sensitive adhesive layer 34 of the pressure-sensitive adhesive sheet 30. For this reason, the depth of the half cut in the cut part 17 and the pressure-sensitive adhesive force of the pressure-sensitive adhesive layer 34 are determined so that the outside region 19B of the cover film 10 can be peeled away from the pressure-sensitive adhesive sheet 30 in the state where the inside region 19A of the cover film 10 remains left together with the carrying member 20 on the pressure-sensitive adhesive sheet 30.

As above, according to the device 2 of the embodiment, the carrying member 20 is retained by the pressure-sensitive adhesive sheet 30 with the outside region 19B of the cover film 10 peeled away from the device 2, whereby the carrying member 20 can stick to the skin 100 together with the pressure-sensitive adhesive sheet 30. Due to no need for such an operation as adjusting the position of the carrying member 20 relative to the pressure-sensitive adhesive sheet 30, drug cannot adhere to the user's fingers.

According to the device 2 of the embodiment, by keeping the carrying member 20 impregnated with a liquid agent as the drug 22, the liquid agent can easily be made into a patch and an advantage is obtained that a liquid agent excellent in release properties and percutaneous absorption properties can be administered as compared with the case of using ointments or tape preparations.

Furthermore, according to the device 2 of the embodiment, the carrying member 20 is folded in the pre-opening state such that the upper layer part 23 and the lower layer part 24 of the carrying member 20 confront the cover film 10 at only their respective surfaces fixed to the cover film 10 and that the upper layer part 23 and the lower layer part 24 confront each other at their respective opposite surfaces. Accordingly, the drug 22 carried on the carrying member 20 can be prevented from sticking to portions of the cover film 10 not holding the carrying member 20. It can thus be suppressed that the dose of the drug 22 is reduced due to adhesion to the cover film 10, thereby effectively achieving the object of the device 2 to percutaneously administer a certain amount of liquid agent to a certain skin area.

Although the present invention has been described by way of the above embodiment, the present invention is not intended to be limited to the above embodiment.

For example, although in the above embodiment an example has been described where a single percutaneous absorption agent carrying member is stored between two layers of the cover film, a plurality of percutaneous absorption agent carrying members may be stored in the two layers of the cover film in the present invention.

Although in the above embodiment an example has been described where two layers of folded percutaneous absorption agent carrying members are superimposed together, two percutaneous absorption agent carrying members may be superimposed in the present invention, with one percutaneous absorption agent carrying member being fixed to one layer of the cover film, with the other percutaneous absorption agent carrying member being fixed to the other layer of the cover film.

4. Variants

Referring to FIGS. 6 to 15D, devices (percutaneous absorption agent delivery devices) according to first to eighth variants will hereinbelow be described. In the first to eighth variants, constituent parts similar to those of the above embodiment will be designated by the same reference numerals in FIGS. 6 to 15D and will not repeatedly be described.

[First Variant and Second Variant]

Figure 6:
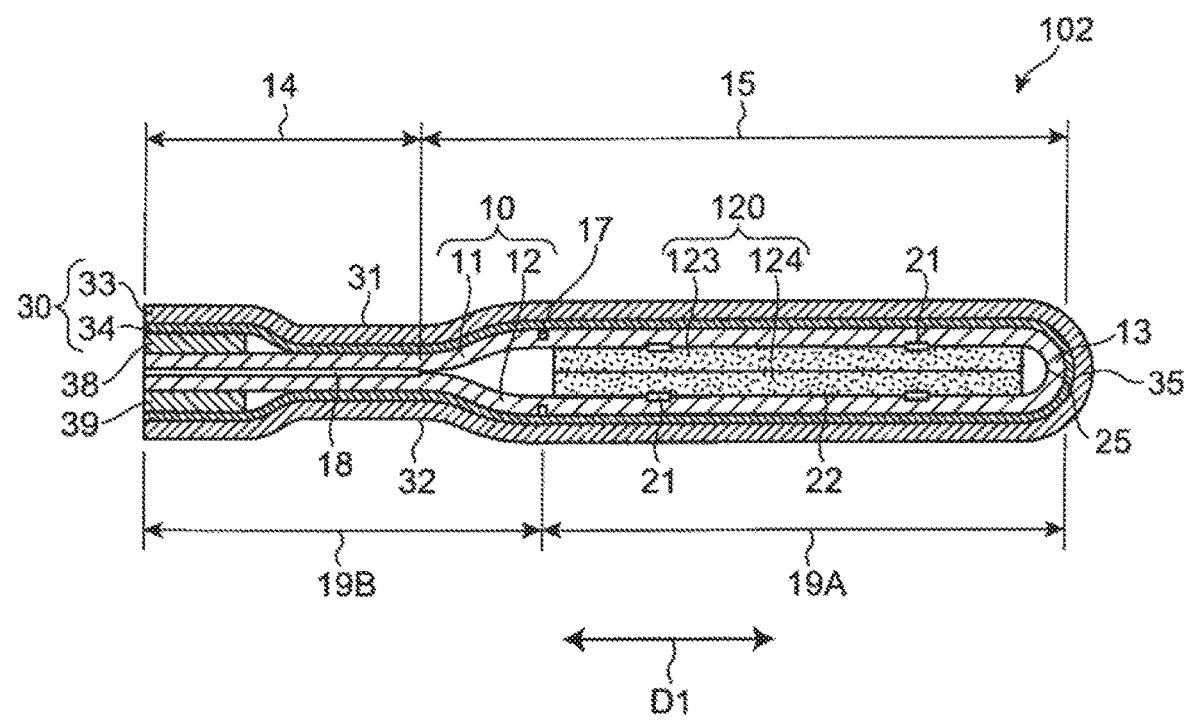
FIG. 6 is a sectional view similar to FIG. 2, showing a first variant of the percutaneous absorption agent delivery device.
Figure 7:
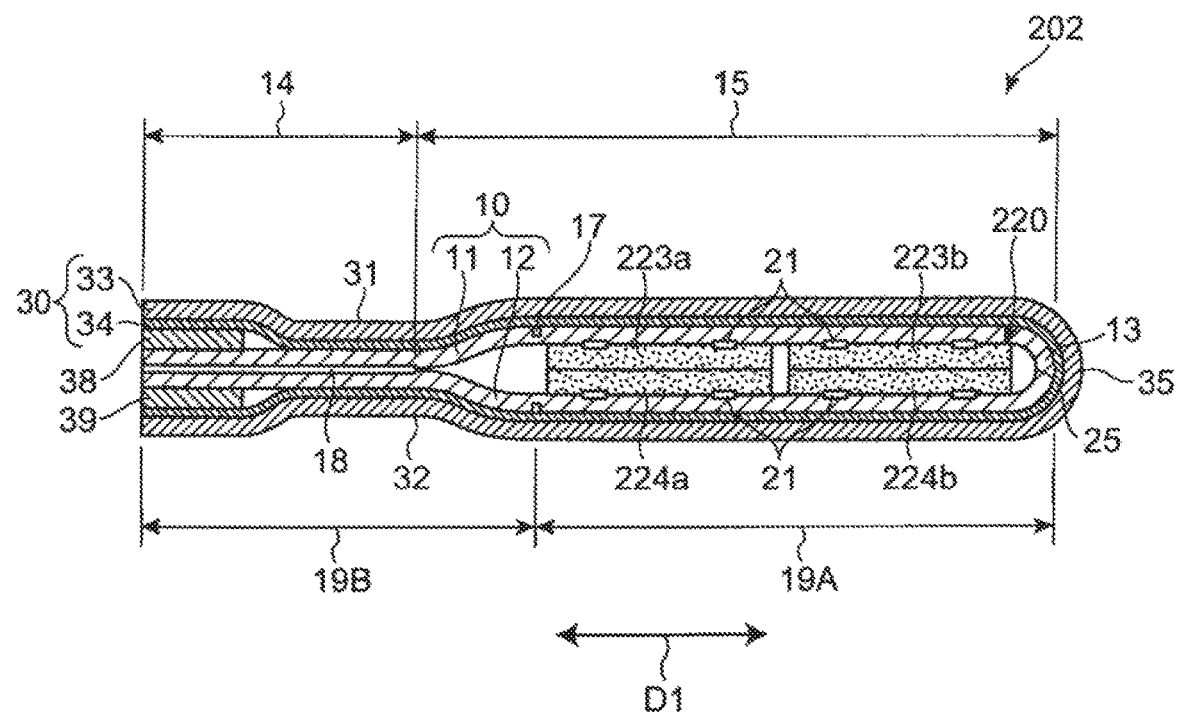
FIG. 7 is a sectional view similar to FIG. 2, showing a second variant of the percutaneous absorption agent delivery device.

FIG. 6 shows a device 102 according to the first variant and FIG. 7 shows a device 202 according to the second variant. In the device 102 shown in FIG. 6, mutually separated two members 123 and 124 are arranged as a carrying member 220 in a superimposed manner, while in the device 202 shown in FIG. 7, four members 223a, 223b, 224a, and 224b are arranged as a carrying member 220, with these members 223a, 223b, 224a, and 224b being superimposed together by two.

As shown in FIGS. 6 and 7, in the first and second variants, two layers (third and fourth layer parts) of the carrying members 120 and 220 are formed by the mutually separated members so that a compact superimposition is feasible in the thickness direction as compared with the case of forming two layers by folding back a less-flexible carrying member. Thus, in the case where the carrying members 120 and 220 are poor in flexibility and are hardly foldable, the third and fourth layer parts may be formed by such mutually independent members so that the devices 102 and 202 having the carrying members 120 and 220 stored compactly into the cover film 10 can be produced.

As shown in FIGS. 6 and 7, in manufacturing the devices 102 and 202 having the third layer parts 123, 223a, and 223b and the fourth layer parts 124, 224a, and 224b configured by the mutually separated carrying members, the carrying members 123, 124, 223a, 223b, 224a, and 224b may be arranged in line symmetry with respect to a center (rectilinear portion forming the first fold 13 extending in the second direction D2) in the first direction D1 of the unfolded cover film 10 and may be fixed to the cover film 10. As a result, when the cover film 10 is folded along the first fold 13, the carrying members 123, 223a, and 223b forming the third layer part and the carrying members 124, 224a, and 224b forming the fourth layer part can mutually be superimposed over the entire surface. Inconsequence, liquid agents permeating into the carrying members 123, 124, 223a, 223b, 224a, and 224b can securely be prevented from adhering to portions of the cover film 10 not holding the carrying members.

In the present invention, in the case of forming the third and fourth layer parts from a plurality of mutually separated carrying members, the number of the carrying members is optional and is not limited to two or four as described above. Note that in case of arranging the carrying members in line symmetry with respect to the unfolded cover film as described above, an even number of carrying members are preferably used so that the carrying members of the third layer part and the carrying members of the fourth layer part are equal in number. It is to be understood that the present invention does not preclude that the carrying members of the third layer part and the carrying members of the fourth layer part are different in number.

Moreover, the present invention does not preclude that a single percutaneous absorption agent carrying member is stored without being folded. Although in this case, challenges for preventing adhesion of drug to the cover film remain left, it can be implemented to reduce the entire size of the device due to reduced sealed regions of the cover film and to reduce the film portions to be discarded in use. In this instance, since the percutaneous absorption agent carrying member is fixed to only one layer of the cover film, only this layer may have the cut part.

[Third Variant]

Figure 8:
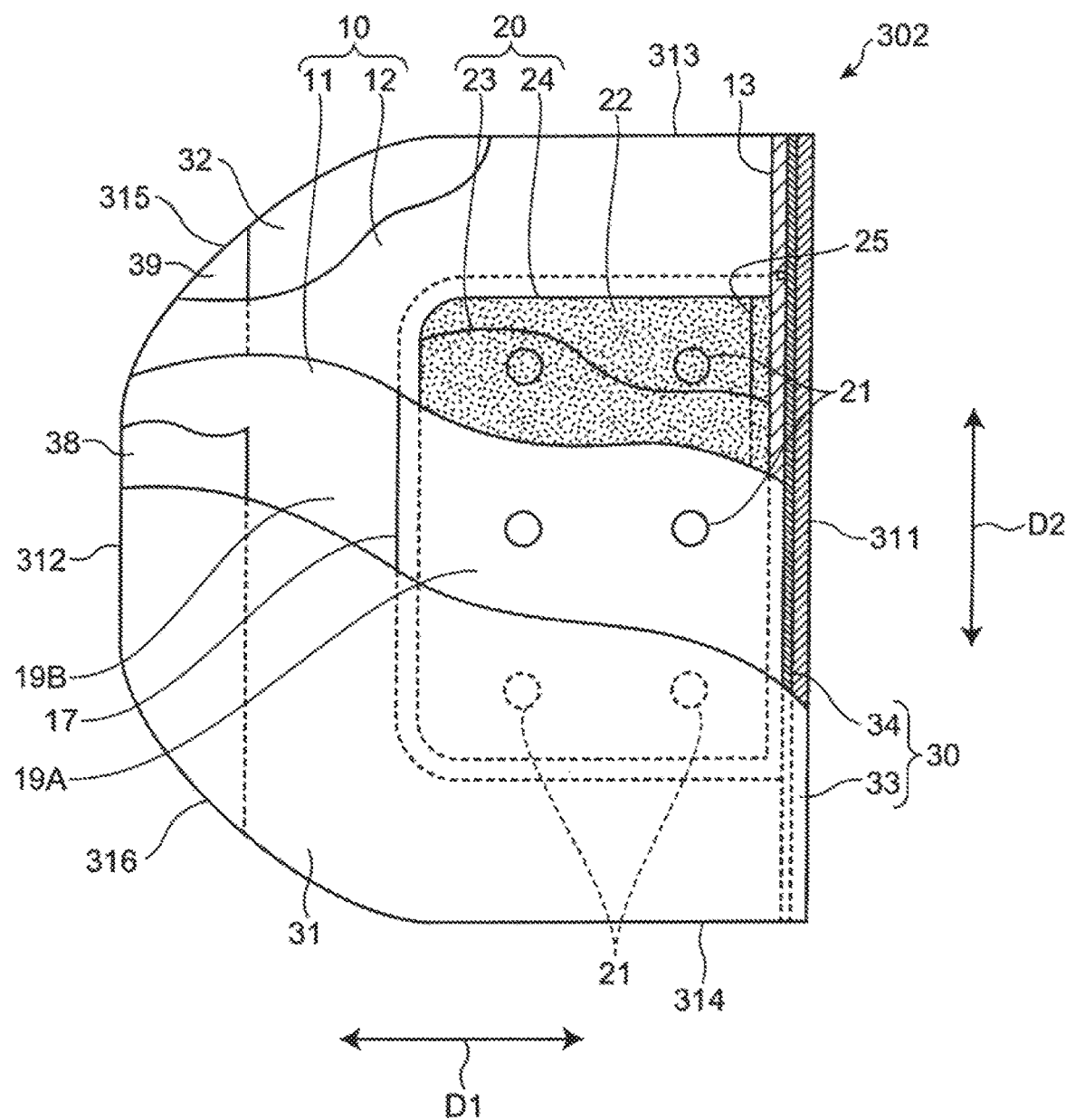
FIG. 8 is a plan view similar to FIG. 1, showing a third variant of the percutaneous absorption agent delivery device.

As shown in FIG. 8, a device 302 according to the third variant comprises: a first edge 311 defining an end toward the fold 13 in the first direction D1 in the folded state; a second edge 312 defining an end opposite to the fold 13 in the first direction D1; a third edge 313 defining one end in the second direction D2; and a fourth edge 314 defining the other end in the second direction D2; and further comprises: a first slant edge 315 cutting away a corner between the second edge 312 and the third edge 313 to join the two edges; and a second slant edge 316 cutting away a corner between the second edge 312 and the fourth edge 314 to join the two edges.

In this manner, the device 302 according to the third variant has two cut-away corners opposite to the fold 13. For this reason, in use, when grasping the edge of the pressure-sensitive adhesive sheet 30 to which the peel-off film 38 is affixed, it is hard in the first slant edge 315 and the second slant edge 316 to grasp the edge of the pressure-sensitive adhesive sheet 30 having the peel-off film 38 affixed thereto. This encourages the pressure-sensitive adhesive sheet 30 to be grasped at the second edge 312, thereby promoting peeling-off of the pressure-sensitive adhesive sheet 30 from the cover film 10 along the first direction D1.

Since the end toward the second edge 312 in the first direction D1 of the cut part 17 formed in the cover film 10 is oriented so as to extend in a direction orthogonal to the first direction D1, the inside region 19A of the cover film 10 can smoothly be separated from the outside region 19B along the cut part 17 disposed orthogonal to the first direction D1 when the pressure-sensitive adhesive sheet 30 is peeled away from the first direction D1 as above (see FIG. 5A).

Figure 9:
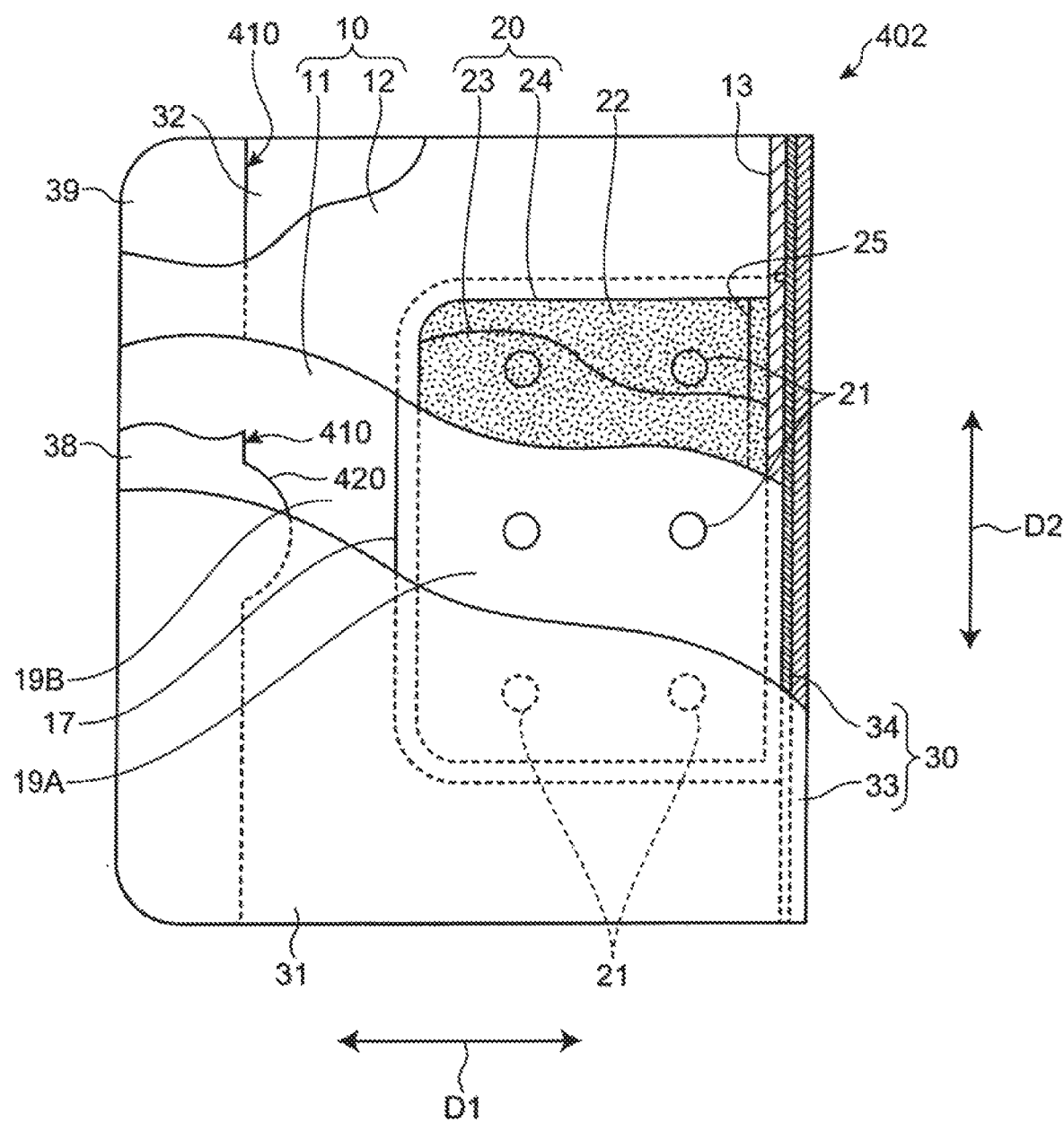
FIG. 9 is a plan view similar to FIG. 1, showing a fourth variant of the percutaneous absorption agent delivery device.

As shown in FIG. 9, in a device 402 according to the fourth variant, ends 410 of the peel-off films 38 and 39 toward the fold 13 in the first direction D1 are formed so as to generally rectilinearly extend along the second direction D2, with the end 410 having at its center in the length direction a bulging part 420 bulging toward the fold 13 in the first direction D1. Although only the bulging part 420 of the peel-off film 38 on one hand is shown in FIG. 9, a similar bulging part 420 is formed on the other peel-off film 39 as well.

Consequently, the peel-off films 38 and 39 can easily be pinched at the above bulging parts 420 when pinching the ends 410 of the peel-off films 38 and 39 in order to peel away the peel-off films 38 and 39 from the pressure-sensitive adhesive layer 34 of the pressure-sensitive adhesive sheet 30, with the outside region 19B of the cover film 10 being removed from the device 402 (see FIG. 5C).

[Fifth Variant]

Figure 10:
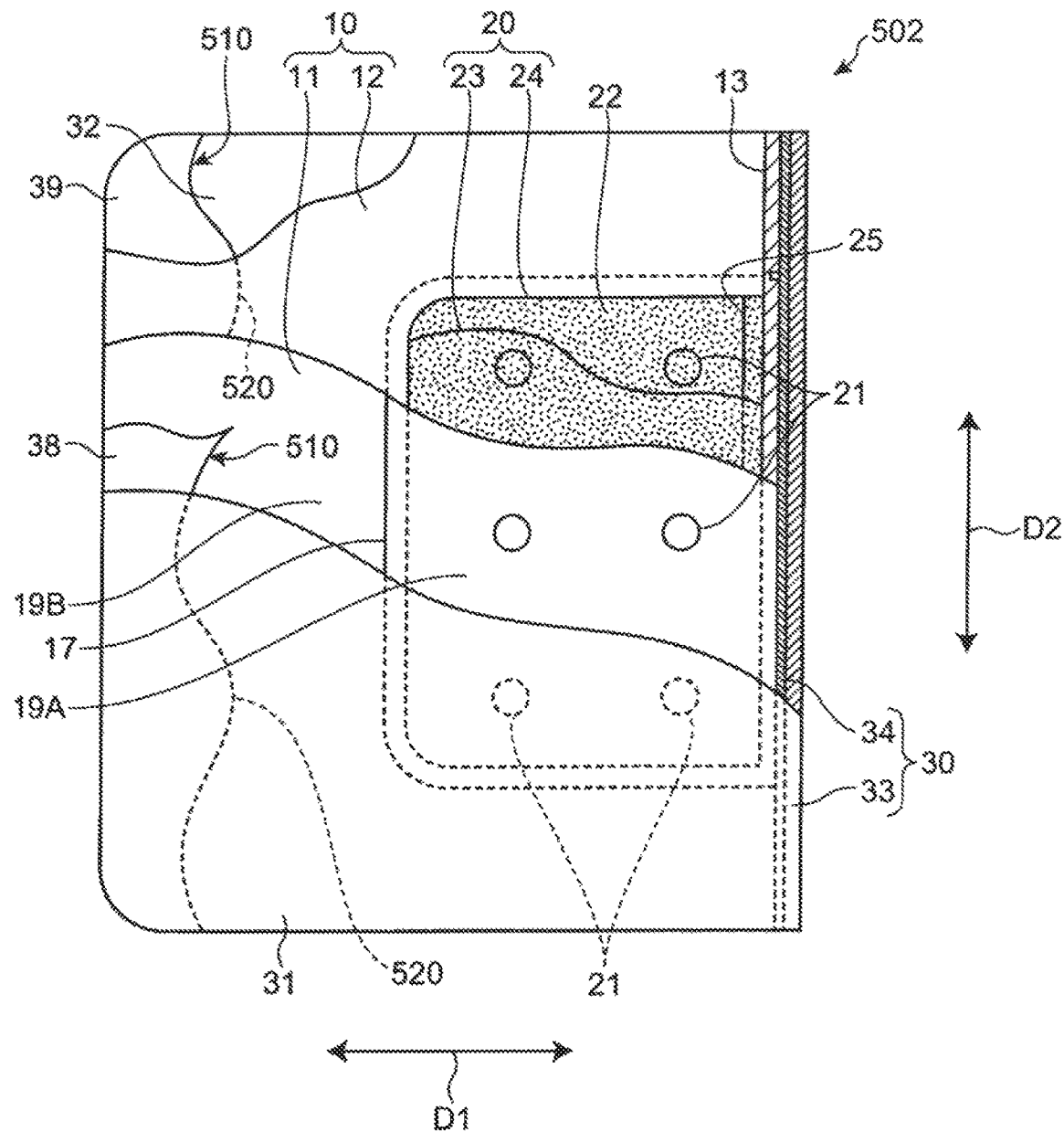
FIG. 10 is a plan view similar to FIG. 1, showing a fifth variant of the percutaneous absorption agent delivery device.

As shown in FIG. 10, in a device 502 according to the fifth variant, ends 510 of the peel-off films 38 and 39 toward the fold 13 in the first direction D1 extend meandering in waves along the second direction D2. The ends 510 of the peel-off films 38 and 39 formed in a wave shape in this manner have bulging parts 520 that bulge toward the fold 13 in the first direction D1. Each of the peel-off films 38 and 39 has a plurality of bulging parts 520 spaced apart in the second direction D2.

Consequently, the peel-off films 38 and 39 can easily be pinched at the above bulging parts 520 when pinching the ends 510 of the peel-off films 38 and 39 in order to peel away the peel-off films 38 and 39 from the pressure-sensitive adhesive layer 34 of the pressure-sensitive adhesive sheet 30, with the outside region 19B of the cover film 10 being removed from the device 502 (see FIG. 5C).

[Sixth Variant]

Figure 11:
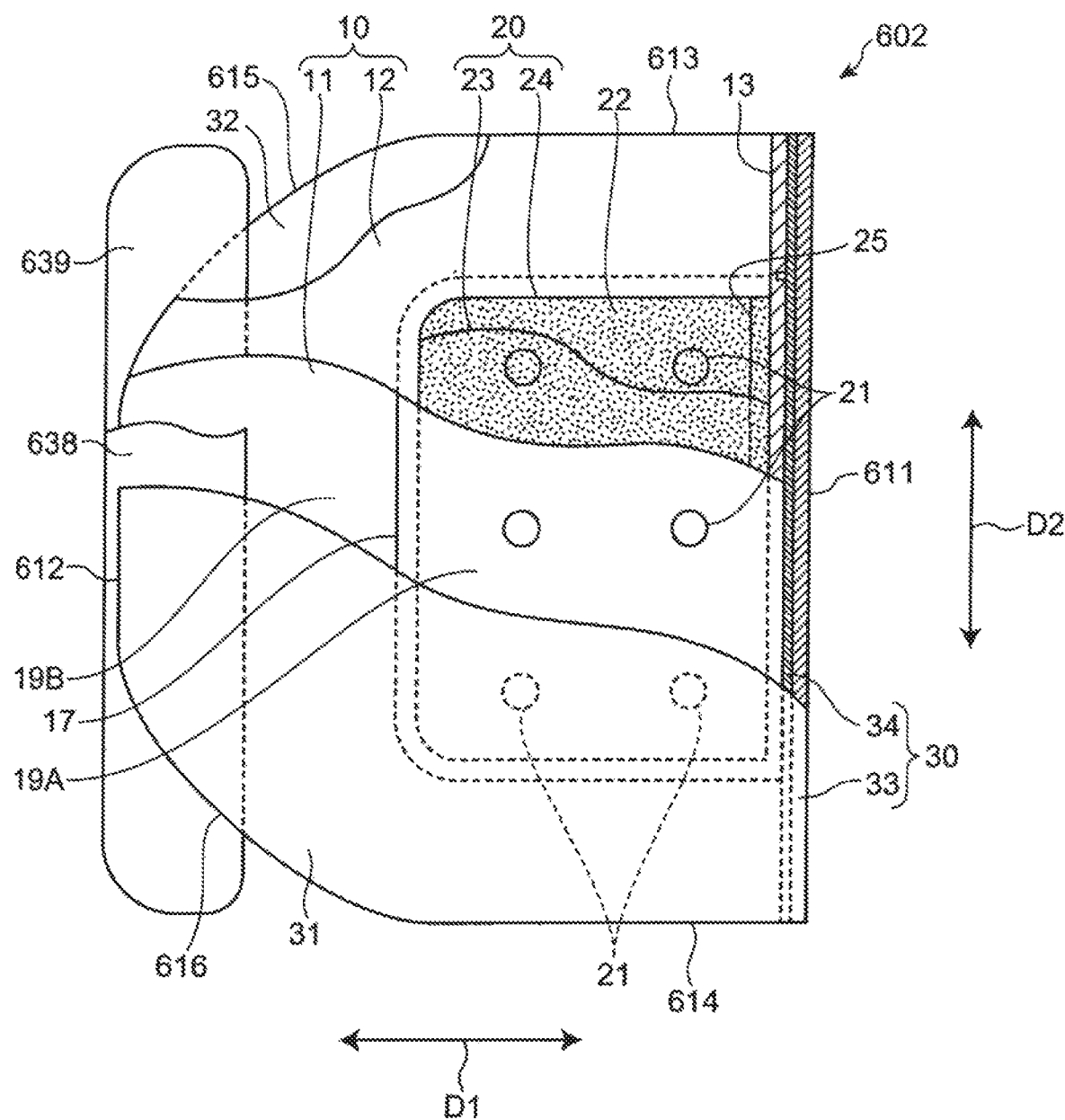
FIG. 11 is a plan view similar to FIG. 1, showing a sixth variant of the percutaneous absorption agent delivery device.

As shown in FIG. 11, a device 602 according to the sixth variant comprises, similar to the device 302 of the third variant shown in FIG. 8, a first edge 611, a second edge 612, a third edge 613, and a fourth edge 614, and further comprises a first slant edge 615 cutting away a corner between the second edge 612 and the third edge 613 to join the two edges and a second slant edge 616 cutting away a corner between the second edge 612 and the fourth edge 614 to join the two edges.

Similar to the above third variant, this encourages the pressure-sensitive adhesive sheet 30 to be grasped at the second edge 612 to be peeled away from the cover film 10 along the first direction D1. Hence, along the cut part 17 oriented orthogonal to the first direction D1, the inside region 19A of the cover film 10 can smoothly be separated from the outside region 19B (see FIG. 5A).

In the sixth variant, the peel-off films 638 and 639 are attached to the pressure-sensitive adhesive layer 34 of the pressure-sensitive adhesive sheet 30 in such a manner as to protrude from the pressure-sensitive adhesive sheet 30. More specifically, the peel-off films 638 and 639 protrude outward from the second edge 612 of the pressure-sensitive adhesive sheet 30 in the first direction D1 and protrude outward from the first slant edge 615 and the second slant edge 616, respectively, in the second direction D2. This facilitates pinching of the peel-off films 638 and 639 at the portions protruding outward from the pressure-sensitive adhesive sheet 30.

Smooth execution is thus ensured of the action (see FIG. 5A) of grasping the edge of the pressure-sensitive adhesive sheet 30 having the peel-off film 638 attached thereto in order to peel away the pressure-sensitive adhesive sheet 30 from the cover film 10 and of the action of pinching the peel-off films 638 and 639 in order to peel off the peel-off films 638 and 639 from the pressure-sensitive adhesive layer 34 of the pressure-sensitive adhesive sheet 30.

[Seventh Variant]

Figure 12:
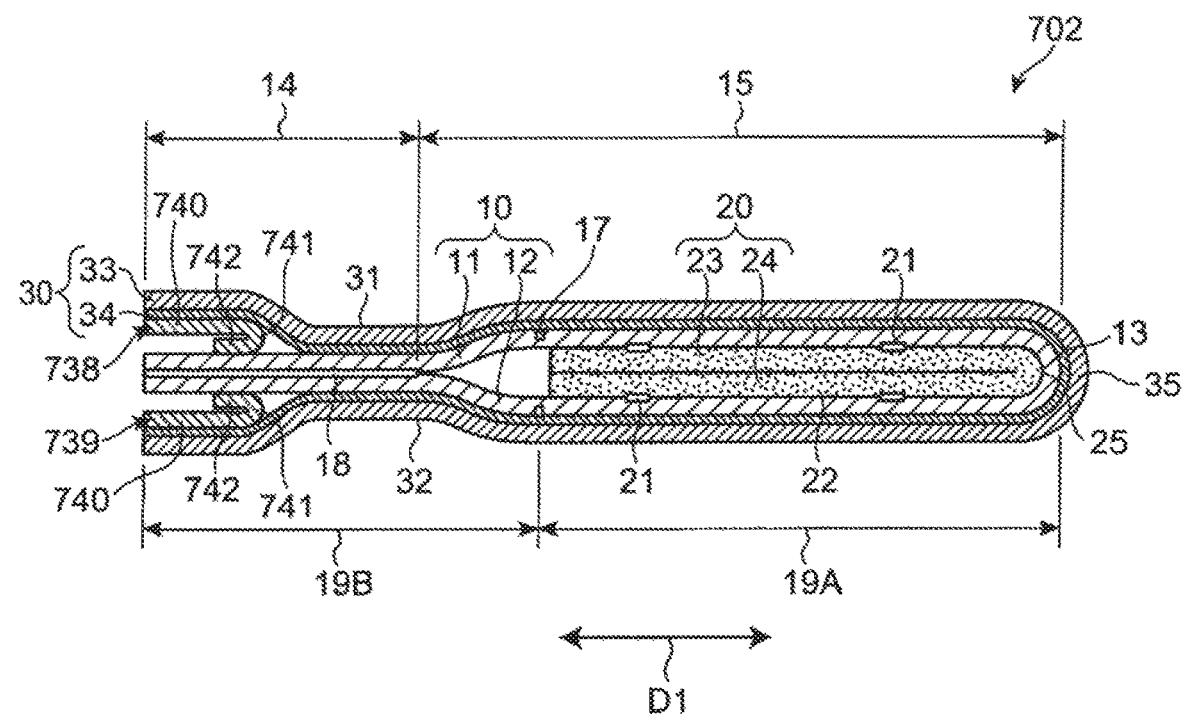
FIG. 12 is a plan view similar to FIG. 1, showing a seventh variant of the percutaneous absorption agent delivery device.

As shown in FIG. 12, in a device 702 according to the seventh variant, peel-off films 738 and 739 intervene, in a bent state, between the cover film 10 and the pressure-sensitive adhesive layer 34 of the pressure-sensitive sheet 30. The peel-off films 738 and 739 each comprise an outer layer part 740 adhered to the pressure-sensitive adhesive layer 34 and an inner layer part 742 continuous to one end of the outer layer part 740 in the first direction D1 via a fold 741 extending in the second direction D2 (see FIG. 1), the inner layer part 742 intervening between the outer layer part 740 and the cover film 10.

The folds 741 of the peel-off films 738 and 739 are arranged opposite to the edges of the pressure-sensitive adhesive sheet 30. The inner layer parts 742 of the peel-off films 738 and 739 are shorter than the outer layer parts 740 in the first direction D1. The inner layer parts 742 are in contact with the outer surfaces of the cover film 10 without being adhered thereto.

Due to the intervention of the inner layer parts 742 of the peel-off films 738 and 739, gaps can easily occur between the outer layer parts 740 of the peel-off films 738 and 739 and the cover film 10. As a result, when peeling away the pressure-sensitive adhesive sheet 30 from the cover film 10 (see FIG. 5A), edges of the pressure-sensitive adhesive sheet 3 having the peel-off films 738 attached thereto can easily be grasped.

Since the inner layer parts 742 of the peel-off films 738 and 739 are not stuck on the pressure-sensitive adhesive sheet 30, the inner layer parts 742 of the peel-off films 738 and 739 can easily be pinched when peeling off the peel-off films 738 and 739 from the pressure-sensitive adhesive sheet 30, contributing to smooth peeling off of the peel-off films 738 and 739.

[Eighth Variant]

Figure 13:
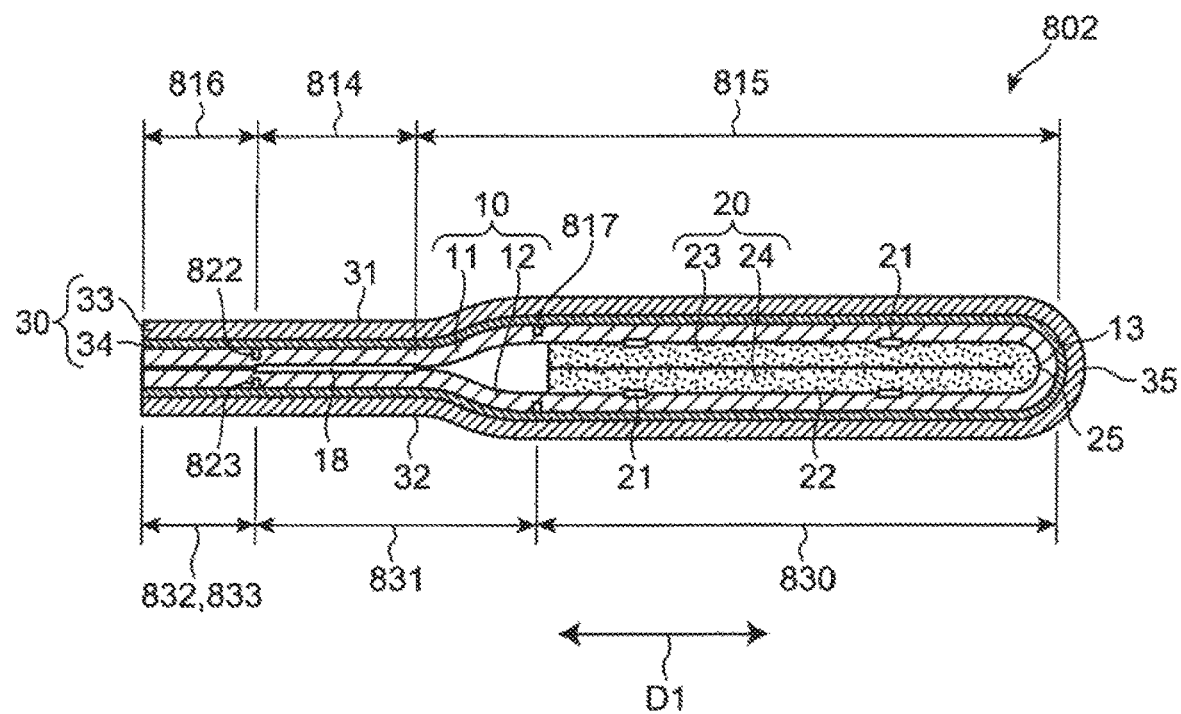
FIG. 13 is a plan view similar to FIG. 1, showing an eighth variant of the percutaneous absorption agent delivery device.

As shown in FIG. 13, a device 802 according to the eighth variant differs from the device 2 (see FIG. 2) of the above embodiment in that the heat seal 18 adhering the upper layer part 11 and the lower layer part 12 of the cover film 10 is not disposed at an end opposite to the fold 13 in the first direction D1.

Figure 14:
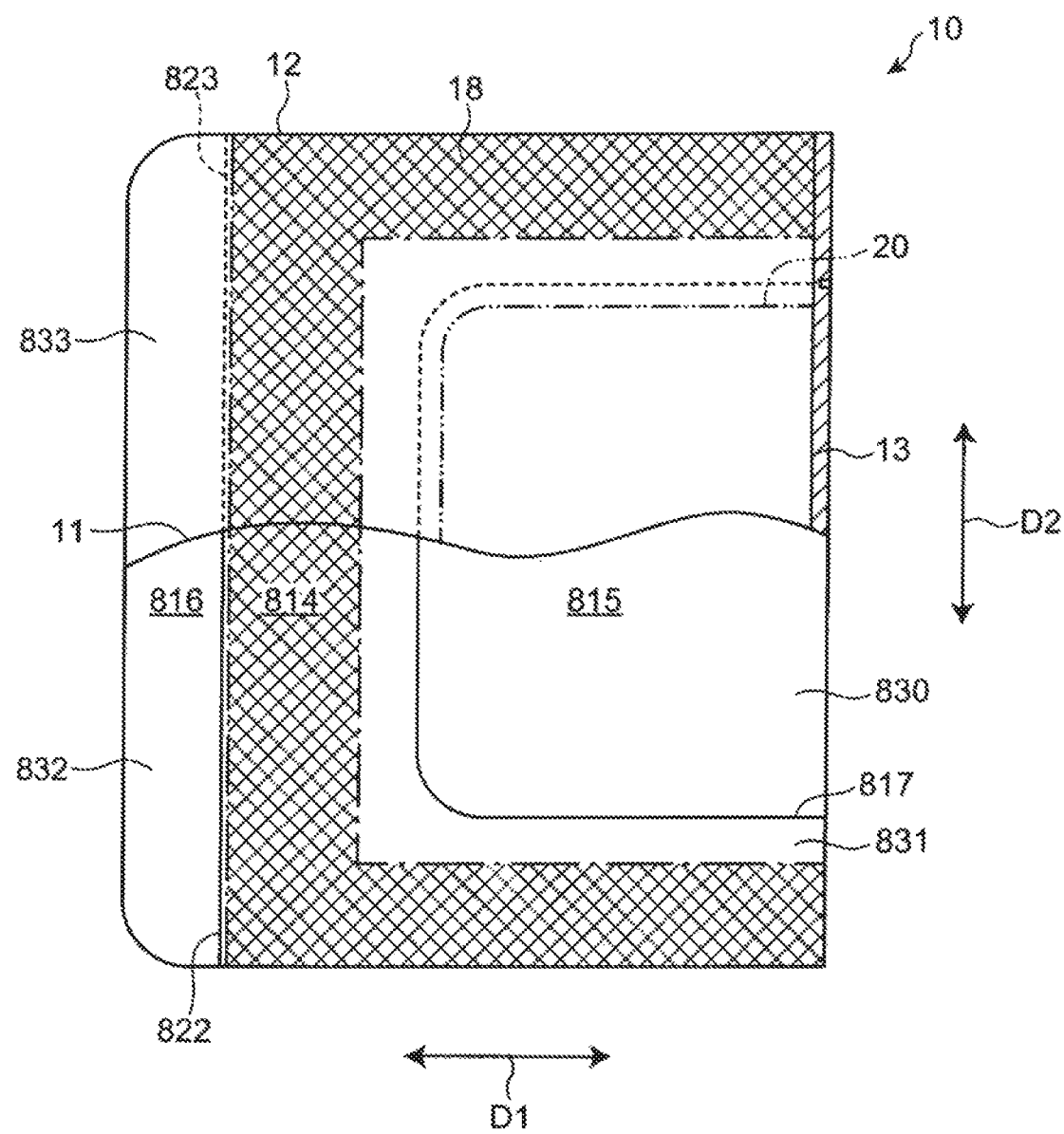
FIG. 14 is a diagram similar to FIG. 3, showing the sealed region and the non-sealed region of the cover film in the percutaneous absorption agent delivery device of the eighth variant.

Hence, as shown in FIG. 14, the eighth variant includes, between the upper layer part 11 and the lower layer part 12 of the cover film 10, a first non-sealed region 815 disposed along the fold 13; a sealed region 814 disposed so as to surround the outer periphery of the first non-sealed region 815 other than portions along the fold 13; and a second non-sealed region 816 disposed between an end opposite to the fold 13 in the first direction D1 and the sealed region 814.

The first non-sealed region 815 is a region corresponding to the non-sealed region 15 (see FIG. 3) in the above embodiment, while the sealed region 814 is a region obtained by excluding the second non-sealed region 816 from the sealed region 14 (see FIG. 3) in the above embodiment. The first non-sealed region 815 is surrounded by the sealed region 814 and the fold 13 over the entire circumference, thus defining a hermetically sealed space in the first non-sealed region 815.

The upper layer part 11 and the lower layer part 12 of the cover film 10 have at portions defining the first non-sealed region 815 a first cut part 817 similar to the cut part 17 (see FIG. 3) of the above embodiment. The carrying member 20 is secured to a portion surrounded by the first cut part 817 in the first non-sealed region 815 of the cover film 10.

The second non-sealed region 816 is open at peripheral parts other than a boundary between the second non-sealed region 816 and the sealed region 814. The upper layer part 11 of the cover film 10 has at a portion defining the second non-sealed region 816 a second cut part 822 extending in the second direction D2 along a boundary between the second non-sealed region 816 and the sealed region 814, while the lower layer part 12 of the cover film 10 has at a portion defining the second non-sealed region 816 a third cut part 823 extending in the second direction D2 along the boundary between the second non-sealed region 816 and the sealed region 814.

The first to third cut parts 817, 822, and 823 may be continuous cuts or intermittent perforations. The first to third cut parts 817, 822, and 823 may be so-called full cuts that extend from one surface up to the other surface of the cover film 10 or may be so-called half cuts leaving without cutting a portion in the vicinity of one surface of the cover film 10. It is preferable for the full cuts to be so-called perforations partially leaving uncut portions. In order to facilitate avoiding evaporation and scattering of the solvent of the percutaneous absorption drug, the first cut part 817 is preferably the half cut. The first cut part 817 shown in FIG. 13 is the half cut extending from the outer surface up to the vicinity of the inner surface of the cover film 10.

The cover film 10 is partitioned into an inside region 830 surrounded by the first cut part 817, a first outside region 831 arranged outside of the first cut part 817 and inside of the second cut part 822 and the third cut part 823, a second outside region 832 arranged outside of the second cut part 822, and a third outside region 833 arranged outside of the third cut part 823.

Similar to the above embodiment, as shown in FIG. 13, the pressure-sensitive adhesive sheet 30 is folded back along the fold 13 of the cover film 10 and is adhered to the outer surface of the upper layer part 11 of the cover film 10 and to the outer surface of the lower layer part 12 thereof. This allows the above first cut part 817, second cut part 822 and third cut part 823 formed on the cover film 10 to be covered from outside by the pressure-sensitive adhesive sheet 30.

Figure 15A:
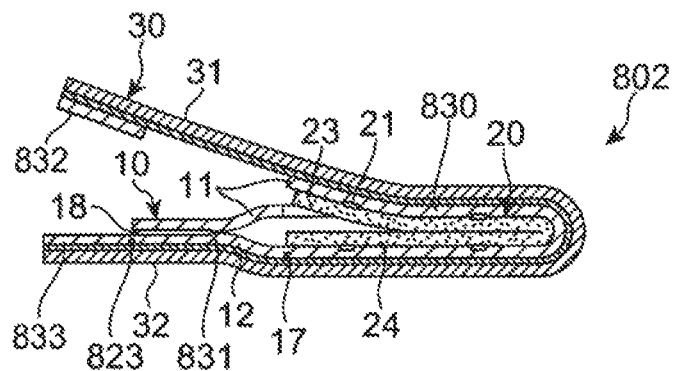
FIG. 15A is a diagram for explaining use of the percutaneous absorption agent delivery device of the eighth variant.

As shown in FIG. 15A, in use of the device 802 of the eighth variant, an edge of the top part 31 for example of the pressure-sensitive adhesive sheet 30 and a portion of the cover film 10 adhered to the edge and defining the second outside region 832 are grasped and the top part 31 of the pressure-sensitive adhesive sheet 30 is peeled away from the upper layer part 11 of the cover film 10 while separating the second outside region 832 along the second cut part 822 (see FIGS. 13 and 14) from the cover film 10.

As a result, the top part 31 of the pressure-sensitive adhesive sheet 30 is peeled off from the first outside region 831 of the upper layer part 11 of the cover film 10, whereas the inside region 830 of the upper layer part 11 is separated along the first cut part 817 from the first outside region 831 and remains left on the pressure-sensitive adhesive sheet 30. The carrying member 20 secured to the inside region 830 of the cover film 10 also remains on the pressure-sensitive adhesive sheet 30 via the inside region 830.

Figure 15B:
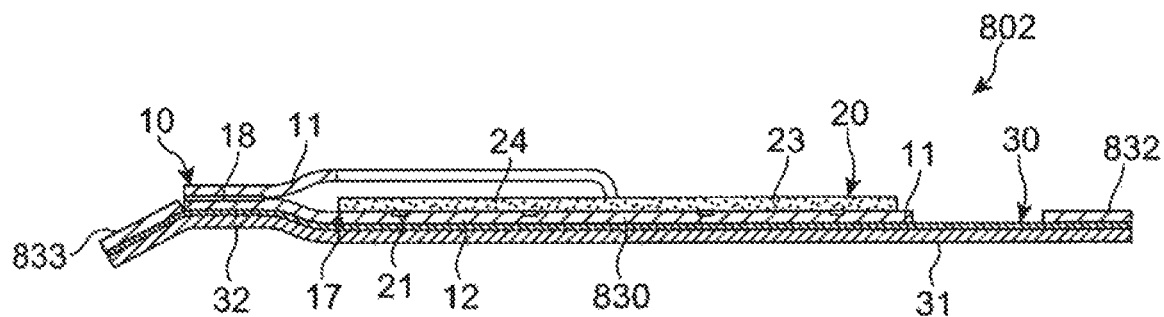
FIG. 15B is a diagram for explaining use of the percutaneous absorption agent delivery device of the eighth variant.

Next, as shown in FIG. 15B, an edge of the bottom part 32 and a portion of the cover film 10 adhered to the edge and defining the third outside region 833 are grasped and the bottom part 32 of the pressure-sensitive adhesive sheet 30 is peeled away from the lower layer part 12 of the cover film 10 while separating the third outside region 833 along the third cut part 823 from the cover film 10.

Figure 15C:
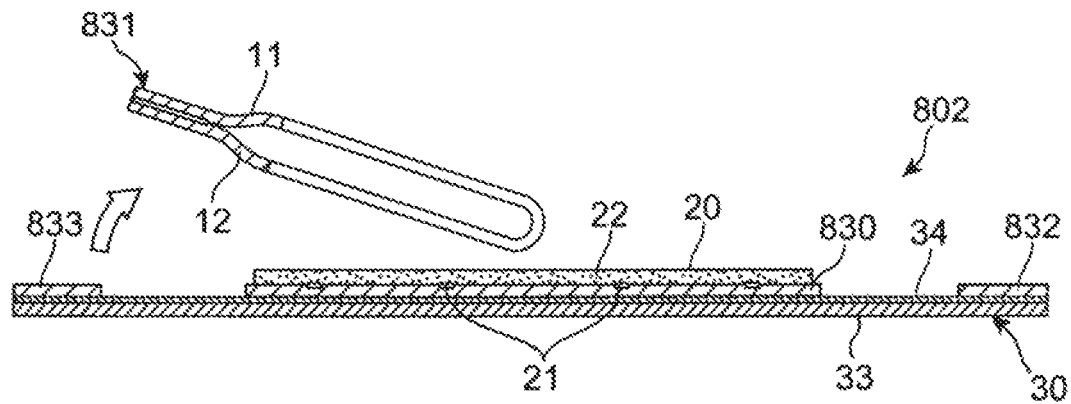
FIG. 15C is a diagram for explaining use of the percutaneous absorption agent delivery device of the eighth variant.

Consequently, as shown in FIG. 15C, the inside region 830 of the cover film 10 is separated from the first outside region 831 over the entire circumference so that the entire first outside region 831 is peeled off from the pressure-sensitive adhesive sheet 30. At this time, over the pressure-sensitive adhesive sheet 30 there remain the inside region 830, second outside region 832, and third outside region 833 of the cover film 10, and the carrying member 20. Over the unfolded pressure-sensitive adhesive sheet 30 there are retained the inside region 830 of the cover film 10 and the carrying member 20 in their respective unfolded states.

Figure 15D:
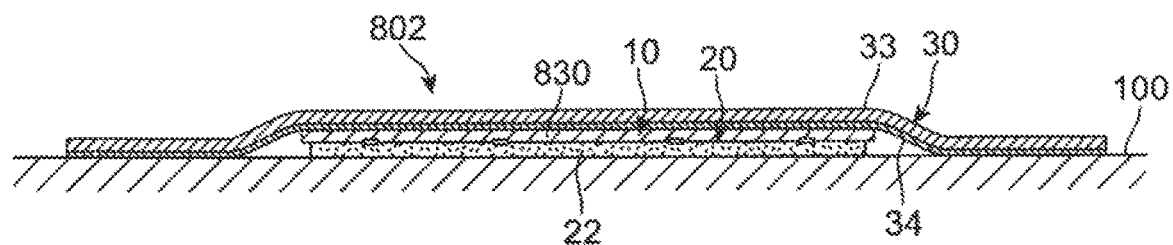
FIG. 15D is a diagram for explaining use of the percutaneous absorption agent delivery device of the eighth variant.

As shown in FIG. 15D, the device 802 with the first outside region 831 of the cover film 10 removed is attached to the skin 100 with the pressure-sensitive adhesive layer 34 being placed on the skin 100. By peeling off the second outside region 832 and third outside region 833 (see FIG. 15C) of the cover film 10 from the pressure-sensitive adhesive layer 34 of the pressure-sensitive adhesive sheet 30, the entire pressure-sensitive adhesive layer 34 can be stuck on the skin 100.

According to the device 802 of the eighth variant, the disposition of the second non-sealed region 816 (see FIGS. 13 and 14) on the cover film 10 allows the second outside region 832 and third outside region 833 of the cover film 10 to fulfill similar functions to those of the peel-off films 38 and 39 (see FIG. 5) in the above embodiment. It is thus possible to use the device 802 with a method similar to that in the above embodiment while achieving a reduction in the number of component parts through the omission of the peel-off films 38 and 39.

EXPLANATIONS OF LETTERS OR NUMERALS

2: percutaneous absorption agent delivery device
10: cover film
11: upper layer part (first layer part, first film part) of cover film
12: lower layer part (second layer part, second film part) of cover film
13: fold (first fold) of cover film
14: sealed region
15: non-sealed region
17: cut part
18: heat seal
19A: inside region
19B: outside region
20: percutaneous absorption agent carrying member
21: heat-bonded part
22: percutaneous absorption drug (drug)
23: upper layer part (third layer part) of percutaneous absorption agent carrying member
24: lower layer part (fourth layer part) of percutaneous absorption agent carrying member
25: fold (second fold) of percutaneous absorption agent carrying member
30: pressure-sensitive adhesive sheet
31: top part (first surface part)
32: bottom part (second surface part)
33: base layer
34: pressure-sensitive adhesive layer
35: fold-back part
38: peel-off film
39: peel-off film
50: manufacturing process
51: cutter
52: carrying member feeder
53: ultrasonic spot welder
54: drug feeder
55: first folding mechanism
56: heat sealer
57: second folding mechanism
58: laminator
59: punching cutter
100: skin
102: percutaneous absorption agent delivery device
120: percutaneous absorption agent carrying member
123: carrying member that defines third layer part
124: carrying member that defines fourth layer part
202: percutaneous absorption agent delivery device
220: percutaneous absorption agent carrying member
223a, 223b: carrying member that defines third layer part
224a, 224b: carrying member that defines fourth layer part
302: percutaneous absorption agent delivery device
315: first slant edge
316: second slant edge
402: percutaneous absorption agent delivery device
420: bulging part of peel-off film
502: percutaneous absorption agent delivery device
520: bulging part of peel-off film
602: percutaneous absorption agent delivery device
638, 639: peel-off film
702: percutaneous absorption agent delivery device
738, 739: peel-off film
740: outer layer part
741: fold
742: inner layer part
802: percutaneous absorption agent delivery device
814: sealed region
815: first non-sealed region
816: second non-sealed region
817: first cut part
822: second cut part
823: third cut part
830: inside region
831: first outside region
832: second outside region
833: third outside region

The invention claimed is:

1. A percutaneous absorption agent delivery device, comprising:
    (a) a solvent-impermeable cover film, the solvent impermeable cover film being folded into first and second layer parts along a fold line such that the first and second layer parts are superimposed with each other, the first and second layer parts being adhered to each other by heat sealing to form a sealing region and a non-sealing region such that, when the cover film is in a folded state, the sealing region extends along three side edges of the folded cover film, other than a remaining side edge along the fold line and, when the cover film is in an unfolded state, the sealing region entirely surrounds the non-sealing region,
        the cover film having a cut that defines an endless cut line that extends along and inside a boundary between the sealing region and the non-sealing region, the endless cut line defining an inside region inside the endless cut line and an outside region outside the endless cut line;
    (b) a percutaneous absorption agent carrying member fixed in the inside region of one major surface of the cover film when the cover film is in the unfolded state such that, when the cover film is changed from the unfolded state to the folded state, the percutaneous absorption agent carrying member is folded along the fold line into first and second member parts that are superimposed with each other; and
    (c) a pressure-sensitive adhesive sheet adhered peelably to an entirety or a part of the other surface of the cover film,
    (d) wherein the cut is designed such that, peeling the pressure sensitive adhesive sheet from an edge opposing the fold line of the folded cover film away from the cover film breaks the cover film at the cut along the endless cut line to separate the pressure sensitive adhesive sheet together with the inside region of the cover film and the percutaneous absorption agent carrying member fixed on the inside region of the cover film from the outside region of the cover film.

2. The percutaneous absorption agent delivery device of claim 1, wherein the cut is a continuous cut.

3. The percutaneous absorption agent delivery device of claim 1, wherein the cut is made of perforations.

4. The percutaneous absorption agent delivery device of claim 1, wherein the cut is a full cut that extends an entirety of a thickness of the cover film.

5. The percutaneous absorption agent delivery device of claim 1, wherein a depth of the cut that extends a part of a thickness of the cover film.

6. The percutaneous absorption agent delivery device of claim 1, wherein
    the percutaneous absorption agent carrying member comprises a third layer part and a fourth layer part that are integrally continuous via a second fold and are superimposed on each other.

7. The percutaneous absorption agent delivery device of claim 6, wherein
    the second fold of the percutaneous absorption agent carrying member is arranged along the first fold of the cover film.

8. The percutaneous absorption agent delivery device of claim 1, wherein
    the percutaneous absorption agent carrying member comprises a third layer part and a fourth layer part that are separate members separate from each other and are superimposed on each other.

9. The percutaneous absorption agent delivery device of claim 6, wherein
    the third layer part and the fourth layer part of the percutaneous absorption agent carrying member are superimposed on each other over the entire surface.

10. The percutaneous absorption agent delivery device of claim 6, wherein
    the third layer part of the percutaneous absorption agent carrying member is superimposed on a portion of the inside of the cut part in the first layer part of the cover film, and wherein
    the fourth layer part the percutaneous absorption agent carrying member is superimposed on a portion of the inside of the cut part in the second layer part of the cover film.

11. The percutaneous absorption agent delivery device of claim 6, wherein
    the third layer part of the percutaneous absorption agent carrying member is secured to the first layer part of the cover film, and wherein
    the fourth layer part of the percutaneous absorption agent carrying member is secured to the second layer part of the cover film.

12. The percutaneous absorption agent delivery device of claim 1, wherein
    the pressure-sensitive adhesive sheet comprises a base layer and a pressure-sensitive adhesive layer disposed on a surface of the base layer confronting the cover film, and wherein
    the pressure-sensitive adhesive layer is adhered peelably to the cover film.

13. The percutaneous absorption agent delivery device of claim 12, comprising:
    a peel-off film arranged between the cover film and the pressure-sensitive adhesive sheet along at least part of an outer peripheral edge of the pressure-sensitive adhesive sheet, the peel-off film being adhered peelably to a pressure-sensitive adhesive surface of the pressure-sensitive adhesive sheet.

14. The percutaneous absorption agent delivery device of claim 1, wherein
    the pressure-sensitive adhesive sheet is folded back along the first fold of the cover film and is adhered to an outer surface of the first layer part of the cover film and to an outer surface of the second layer part thereof.

15. The percutaneous absorption agent delivery device of claim 1, wherein
    the cover film is an aluminum laminate film.

* * * * *